(12) United States Patent
Cullen et al.

(10) Patent No.: US 6,261,772 B1
(45) Date of Patent: Jul. 17, 2001

(54) METHOD OF ASSAYING FOR RNA: PROTEIN INTERACTIONS

(75) Inventors: Bryan R. Cullen, Durham, NC (US); Wade S. Blair, Clinton, CT (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 09/239,523

(22) Filed: Jan. 29, 1999

Related U.S. Application Data

(60) Provisional application No. 60/073,224, filed on Jan. 30, 1998.

(51) Int. Cl.$^7$ .................................................. C12Q 1/68
(52) U.S. Cl. ............................. 435/6; 435/7.2; 435/7.21; 536/23.1; 536/24.1
(58) Field of Search .................. 435/6, 7.2, 7.21; 536/23.1, 24.1

(56) References Cited

U.S. PATENT DOCUMENTS

| | | | |
|---|---|---|---|
| 5,283,173 | 2/1994 | Fields et al. | 435/5 |
| 5,468,614 | 11/1995 | Fields et al. | 435/6 |
| 5,580,722 | 12/1996 | Foulkes et al. | 435/6 |
| 5,610,015 | 3/1997 | Wickens et al. | 435/6 |

OTHER PUBLICATIONS

Southgate et al, "Activation of transcription by HIV–1 Tat protein tethered to nascent RNA through another protein", Nature 345:640–642 (1990).

Selby and Peterlin, "Trans–Activation by HIV–1 Tat via a Heterologous RNA Binding Protein", Cell 62:769–776 (1990).

Tiley et al, "The VP16 transcription activation domain is functional when targeted to a promoter–proximal RNA sequence", Genes & Development 6:2077–2087 (1992).

Madore et al, "Sequence Requirements for Rev Multimerization in Vivo", Virology 202:186–194 (1994).

Blair et al, "Utilization of a mammalian cell–based RNA binding assay to characterize the RNA binding properties of picornavirus 3C proteinases", RNA 4:215–225 (1998).

Tan and Frankel, "A novel glutamine–RNA interaction identified by screening libraries in mammalian cells", Proc. Natl. Acad. Sci. USA 95:4247–4252 (1998).

Jain and Belasco, "A Structural Model for the HIV–1 Rev–RRE Complex Deduced from Altered–Specificity Rev Variants Isolated by a Rapid Genetic Strategy", Cell 87:115–125 (1996).

Hoffmann and Willbold, "A Selection System to Study Protein–RNA Interactions: Functional Display of HIV–1 Tat Protein on Filamentous Bacteriophage M13", Biochemical and Biophysical Research Communications 235:806–811 (1997).

Sagesser et al, "Detection and isolation of RNA–binding proteins by RNA–ligand screening of a cDNA expression library", Nucleic Acids Research 25(19):3816–3822 (1997).

Wilhelm et al, "A one–hybrid system for detecting RNA–protein interactions", Genes to Cells 1(3):317–324 (1996), Database BIOSIS, No. 199699184390.

*Primary Examiner*—Remy Yucel
(74) *Attorney, Agent, or Firm*—Nixon & Vanderhye P.C.

(57) ABSTRACT

The present invention relates, in general to an assay method, and, in particular, to an in vivo method of assaying the interaction of RNA with proteins. The invention relates to a kit suitable for use in connection with such method.

21 Claims, 16 Drawing Sheets

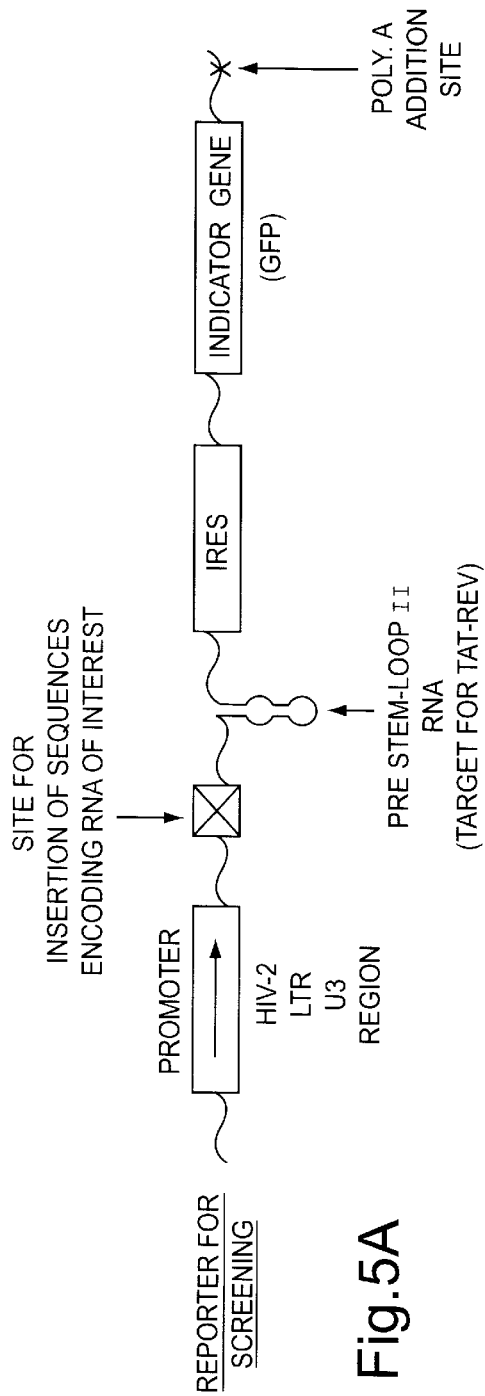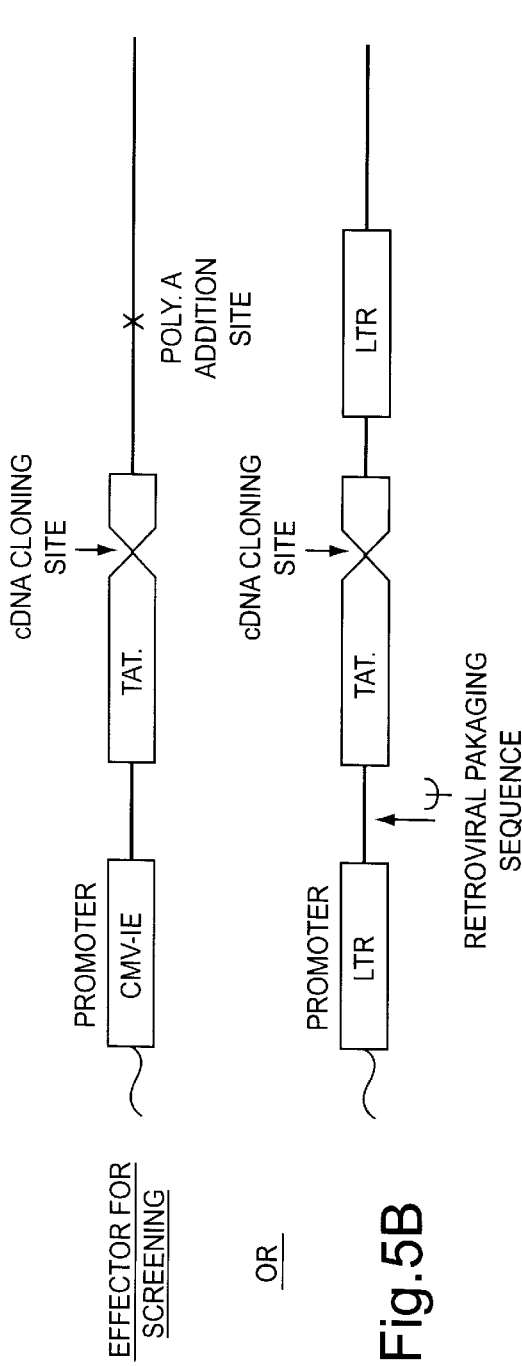

SEQUENCE LISTING

<160> NUMBER OF SEQ ID NOS: 4

<210> SEQ ID NO: 1
<211> LENGTH: 43
<212> TYPE: DNA
<213> ORGANISM: Artificial Sequence
<220> FEATURE:
<223> OTHER INFORMATION: Description of Artificial Sequence:primer
<221> NAME/KEY: primer_bind
<222> LOCATION: (19)..(25)
<223> OTHER INFORMATION: N can be A, C, G, T, Unknown or Other

```
<400> SEQUENCE: 1
cccccggatc cactaaccnn nnnnnggagg gccgtcaaag cta          43

<210> SEQ ID NO: 2
<211> LENGTH: 43
<212> TYPE: DNA
<213> ORGANISM: Artificial Sequence
<220> FEATURE:
<223> OTHER INFORMATION: Description of Artificial Sequence:primer
<221> NAME/KEY: primer_bind
<222> LOCATION: (19)..(25)
<223> OTHER INFORMATION: N can be A, C, T, G, Unknown or Other

<400> SEQUENCE: 2
tagctttgac ggccctccnn nnnnnggtta gtggatccgg ggg          43

<210> SEQ ID NO: 3
<211> LENGTH: 91
<212> TYPE: RNA
<213> ORGANISM: Artificial Sequence
<220> FEATURE:
<223> OTHER INFORMATION: Description of Artificial Sequence:PV1 RNA

<400> SEQUENCE: 3
uuaaaacagc ucugggguug uacccacccc agaggcccac guggcggcua guacuccggu    60
auugcgguac ccuuguacgc cuguuuuaua c                                   91

<210> SEQ ID NO: 4
<211> LENGTH: 154
<212> TYPE: RNA
<213> ORGANISM: Artificial Sequence
<220> FEATURE:
<223> OTHER INFORMATION: Description of Artificial Sequence:MPMV CTE RNA
      element

<400> SEQUENCE: 4
agacuggaca gccaaugacg gguaagagag ugacauuucu cacuaaccua agacaggagg    60
gccgucaaag cuacugccua auccaaugac ggguaauagu gacaagaaau guaucacucc   120
aaccuaagac aggcgcagcc uccgagggau gugu                              154
```

US 6,261,772 B1

METHOD OF ASSAYING FOR RNA: PROTEIN INTERACTIONS

Figure 1A:
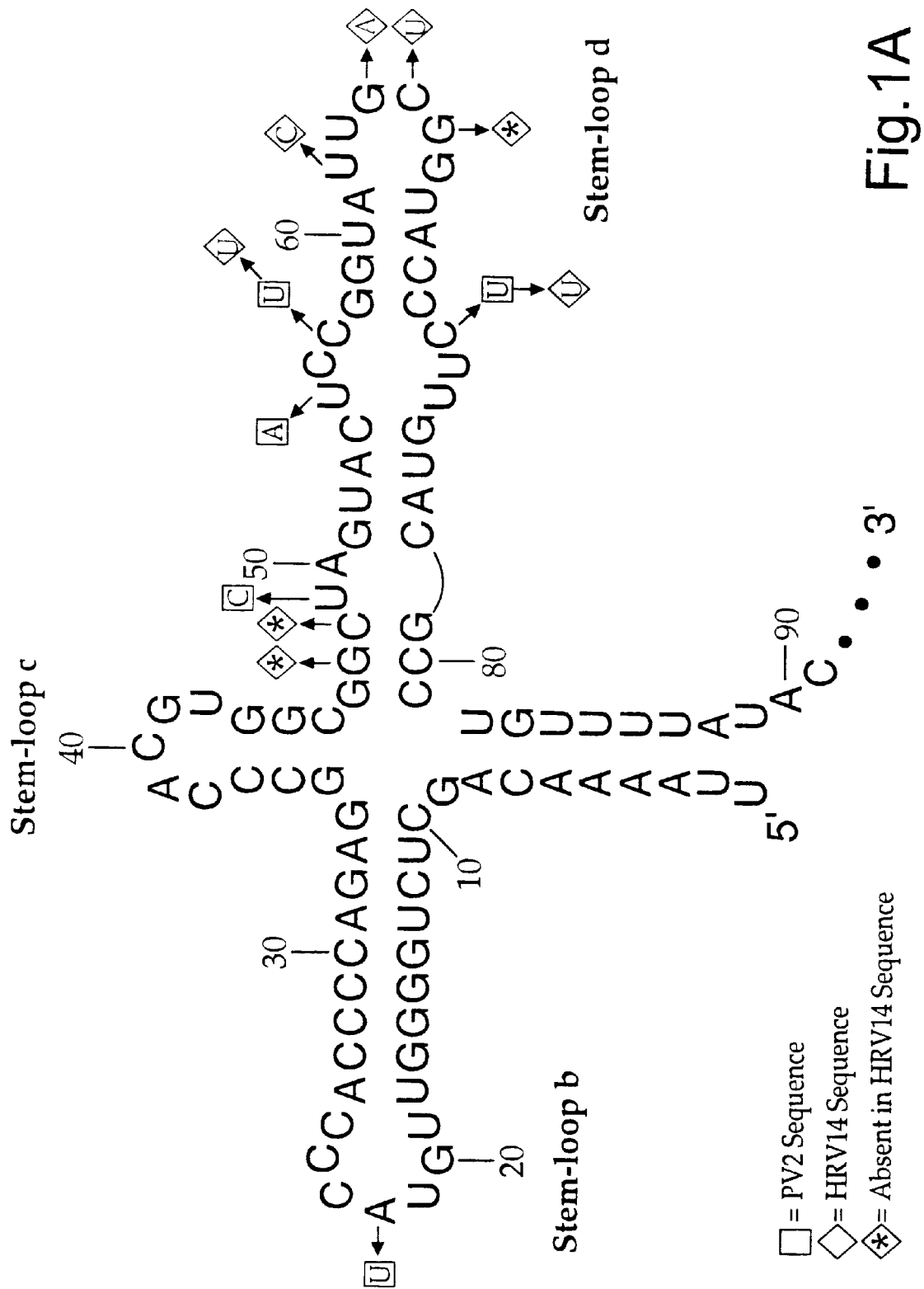

This application claims priority from Provisional Application No. 60/073,224, filed Jan. 30, 1998; the entirety of the Provisional Application is incorporated herein by reference.

This invention was made with Government support under AI35372 awarded by the National Institutes of Health. The Government has certain rights in the invention.

TECHNICAL FIELD

The present invention relates, in general, to a method of assaying an RNA:protein interaction. The invention further relates to a kit suitable for use in such a method.

BACKGROUND OF THE INVENTION

RNA:protein interactions regulate many aspects of the growth and metabolism of mammalian cells and, in particular, regulate critical stages in the replication of many pathogenic human viruses. The investigation of such binding events, however, has historically been restricted largely to in vitro, that is, cell free, assays that may not always be able to recapitulate in vivo interactions accurately. A three hybrid system for measuring RNA:protein interactions in vivo has been described (SenGupta et al, Proc. Natl. Acad. Sci. USA 93:8496 (1996)). The system used, however, is a yeast system. As a result, specific protein post-translational modifications that may be critical for RNA binding in mammalian cells, and that may not be possible in the yeast system, may not occur as normal. Further, any mammalian cofactors required for RNA binding, may not be expressed in the yeast system.

The present invention provides a mammalian-cell based RNA binding assay useful for the effective demonstration and characterization of numerous RNA:protein interactions. The effectiveness of the assay is exemplified by the use of the system to characterize the interaction of picornavirus 3C proteases with their cognate RNA target sequences in vivo, and to characterize the interaction of Mason-Pfizer Monkey Virus (MPMV) constitutive transport element (CTE) mutants with human Tap protein.

Picornaviruses contain a positive-sense RNA genome of ~7500 nt that is translated into a single polyprotein and are therefore dependent on proteolytic processing by virally encoded proteinases for the generation of mature viral gene products (Dougherty et al, Microbial. Rev. 57:781–822 (1993)). The majority of cleavage events are mediated by the 3C proteinase or one of its precursors, 3CD, which consists of the viral RNA polymerase (3D) fused to the 3C proteinase (Hanecak et al, Proc. Natl. Acad. Sci. USA 79:3973–3977 (1982); Jore et al, J. Gen. Virol. 69:1627–1636 (1988); Ypma-Wong et al, Virology 166:265–270 (1988)). 3C cleaves primarily at Gln-Gly amino acid pairs, but additional primary sequence determinants (Nicklin et al, Biotechnology 4:36–42 (1986); Pallai et al, J. Biol. Chem. 264:9738–9741 (1989); Blair et al, J. Virol. 65:6111–6123 (1991)) and structural determinants (Ypma-Wong et al, J. Biol. Chem. 63:17846–17856 (1988b)) are required for efficient substrate recognition and cleavage by 3C activity.

In addition to its vital role as a proteinase, 3C is thought to have a key role in viral RNA replication. Picornaviruses are characterized by a large (~750 nt) 5' noncoding region (5' NCR), which contains sequences that direct the efficient translation of picornaviral RNAs (the internal ribosome entry site or IRES) (Pelletier et al, Nature 334:320–325 (1988); Jang et al, J. Virol. 62:2636–2643 (1988); for review, see Ehrenfeld et al, Curr. Topics Microbiol. Immunol 203:65–83 (1995)) as well as sequence elements that are required for viral RNA replication (Andino et al, Cell 63:369–380 (1990); Borman et al, EMBO J. 13:3149–3157 (1994); Shiroki et al, J. Virol. 69:6825–6832 (1995)). 3C-containing ribonucleoprotein (RNP) complexes that are required for viral replication have been proposed to form on the 5' NCRs of at least three picornaviruses, i.e. poliovirus, rhinovirus and hepatitis A virus (Andino et al, Cell 63:369–380 (1990); Leong et al, Virology 89:484–493 (1993); Kusov et al, RNA 3:291–302 (1997)). The biological relevance of this RNP complex is most evident for poliovirus and is supported by the following genetic and biochemical data: 1) 3CD can be detected in RNA replication complexes in poliovirus infected cells (Lundquist et al, Virology 89:484–493 (1978); Dasgupta et al, Proc. Natl. Acad. Sci. USA 76:2679–2683 (1979)); 2) poliovirus 3CD forms stable RNP complexes with the 5' terminal sequences of its cognate genomic RNA in vitro (Andino et al, Cell 63:369–380 (1990); 3) site-specific mutations in the 5' terminal sequences of poliovirus RNA which affect 3CD RNP complex formation in vitro result in RNA replication defects in vivo (Andino et al, Cell 63:369–380 (1990); Andino et al, EMBO J. 12:3587–3598 (1993)); 4) amino acid substitution mutations in poliovirus 3C sequences have been described that affect viral RNA replication rather than 3C-mediated protein processing in vivo (Dewalt et al, In: Semler & Ehrenfeld, eds., Molecular Aspects of Picornavirus Infection and Detection (1989); Blair et al, Virology 218:1–13 (1996)); and, 5) a mutation in 5' terminal sequences of poliovirus genomic RNA that affects viral RNA replication can be suppressed by pseudoreversion mutations in 3C proteinase sequences (Andino et al, J. Virol. 64:607–612 (1990)). Therefore, poliovirus 3C, and most likely other picornavirus 3C proteinases, play a direct role in viral RNA replication that is distinct from their role in protein processing.

The 3CD proteinase derived from poliovirus type 1 (PV1) has been shown to specifically interact in vitro with a cloverleaf-like RNA secondary structural element located in the 5' terminal ~100 nt of poliovirus genomic RNA (FIG. 1A) (Andino et al, Cell 63:369–380 (1990)). Efficient PV1 3CD/RNA complex formation in vitro depends on the presence of a cellular protein of approximately 36 kDa in size (p36) (Andino et al, Cell 63:369–380 (1990), Andino et al, EMBO J. 12:3587–3598 (1993)) or additional viral polypeptides (i.e., 3AB) (Harris et al., J. Biol. Chem. 269:27004–27014 (1994); Xiang et al, J. Virol. 69:3658–3667 (1995)). Genetic and biochemical studies indicate that the p36 cellular protein interacts with stem-loop b, while. 3CD interacts with stem-loop d within the predicted cloverleaf-like RNA secondary structural element (Andino et al, EMBO J. 12:3587–3598 (1993)). Similarly, human rhinovirus 14 (HRV14) 3C interacts with stem-loop d within the corresponding RNA cloverleaf secondary structure element present at the 5' terminus of rhinovirus genomic RNA (Walker et al, J. Biol. Chem. 270:14510–14516 (1995)). However, in contrast to PV1 3CD, HRV14 3C interacts efficiently with its RNA target in vitro in the absence of additional viral or cellular polypeptides (Leong et al, Virology 89:484–493 (1993); Walker et al, J. Biol. Chem. 270:14510–14516 (1995)). Furthermore, PV1 3CD exhibits a low affinity for RNA sequences derived from the 5' terminus of HRV 14 genomic RNA (Xiang et al, J. Virol. 69:3658–3667 (1995)), while HRV14 3C exhibits similar affinities for both PV1 and HRV14 5' terminal sequences in vitro (Walker et al, J. Biol. Chem. 270:14510–14516

(1995)). Consistent with these latter observations, poliovirus RNA replication in vivo is inhibited by substitution of HRV14 5' NCR sequences containing stem-loop d (Rohll et al, J. Virol. 68:4284–4391 (1994)). In contrast, chimeric PV1/HRV14 genomic RNAs containing the PV1 NCR and encoding an HRV 14 polyprotein replicate efficiently (Todd et al, Virology 229:90–97 (1997)). Therefore, although the PV1 and HRV14 3C proteinases exhibit similar RNA binding properties, differences exist in RNA target specificity and/or the requirements for 3C RNP complex formation. Using the in vivo RNA:protein binding assay of this invention it has been possible to further characterize the interaction of 3C with picornavirus RNA sequences in mammalian cells and to demonstrate that the poliovirus and rhinovirus 3C proteinases are in fact sufficient to bind to 5' terminal sequences derived from their respective genomic RNAs in vivo.

As indicated above, the effectiveness of the present assay has been exemplified by the use of the system to characterize the interaction of MPMV CTE mutants with human Tap protein. CTE encoded by simian type D retroviruses directs unspliced viral RNAs into a sequence-specific nuclear RNA export pathway that is at least in part similar to the pathway used by cellular mRNAs. The human Tap protein has been shown to bind the CTE, and to enhance CTE function in semi-permissive Xenopus oocytes, and has therefore been proposed as a CTE cofactor. Using the in vivo assay of the invention, it has been possible to demonstrate that the ability of the CE mutants to bind Tap closely correlates with their function in both human cells and in human Tap expressing avian cells. Using the present assays, it has also been possible to define a novel sequence-specific RNA binding motif of the Tap protein that is sufficient for CTE binding but not adequate to rescue CTE function; the isolated Tap RNA binding domain in fact acts as a dominant negative inhibitor of full-length Tap.

SUMMARY OF THE INVENTION

The present invention relates to a method of detecting RNA:protein interactions in vivo. The method depends on the activation of a promoter (e.g., the HIV-1 LTR promoter) by a RNA targeted Tat protein. The invention further relates to constructs suitable for use in such a method and to a kit comprising same.

BRIEF DESCRIPTION OF THE INVENTION

Figure 1B:
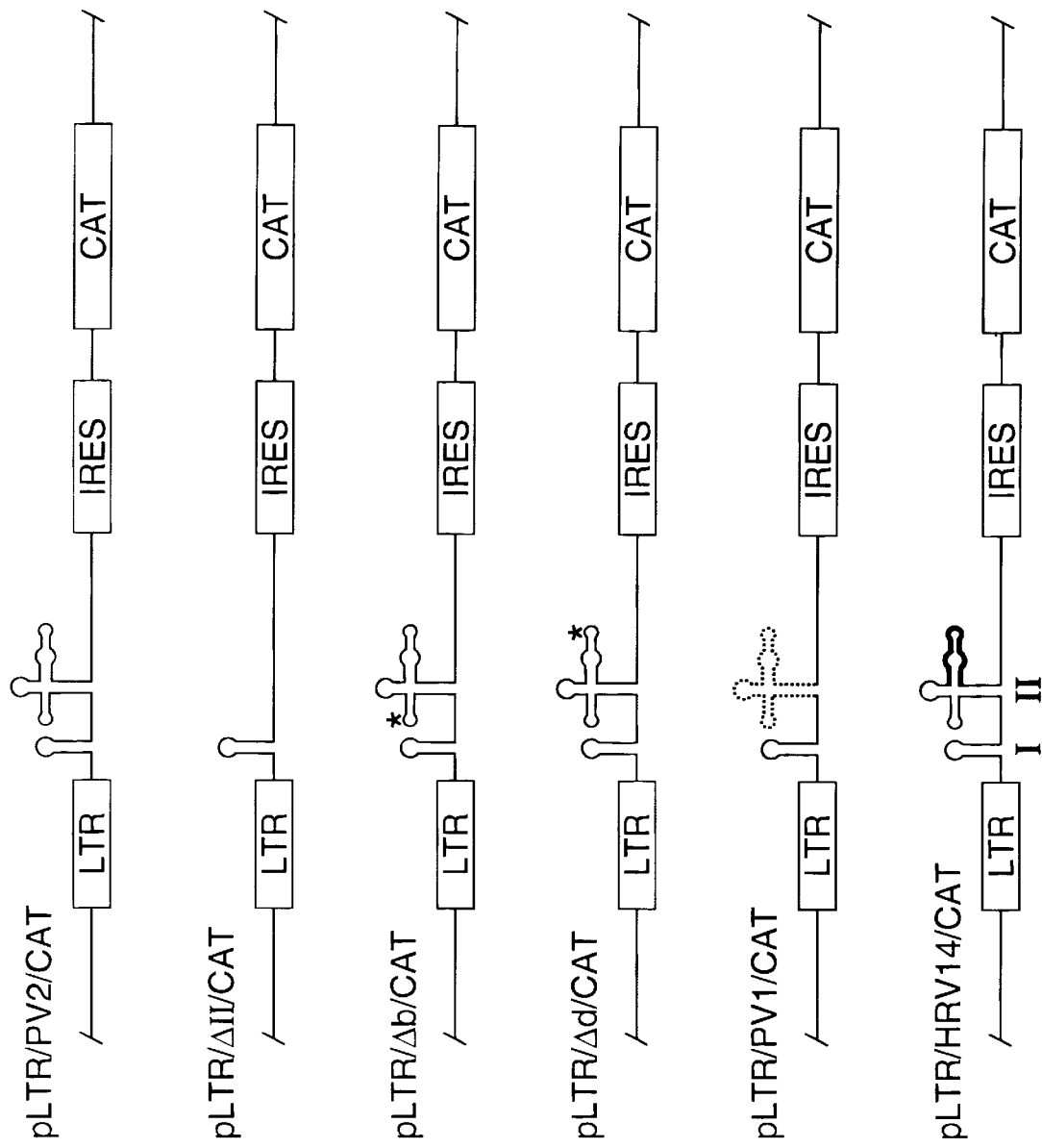

FIGS. 1A and 1B. Structures of CAT reporter constructs. (FIG. 1A) The predicted RNA cloverleaf secondary structure formed by the first 91 nucleotides of PV1 genomic RNA is shown (SEQ ID. NO:3). Nucleotide differences in the corresponding RNA stem-loop in PV2 are boxed while differences between PV1 and HRV14, in stem-loop d only, are indicated by diamonds. (FIG. 1B) Each reporter encodes the CAT gene preceded by sequences corresponding to the PV2 5' NCR. Expression of each reporter is controlled by an HIV-1 LTR promoter derivative that contains RNA target sequences for the HIV-1 Rev protein in place of TAR (I). The location of the RNA cloverleaf structure of PV2 is indicated (II). Reporter constructs were derived from the parental pLTR/PV2/CAT plasmid by deletion or mutation of this secondary structure or by substitution of equivalent sequences derived from PV1 or HRV14.

Figure 2:
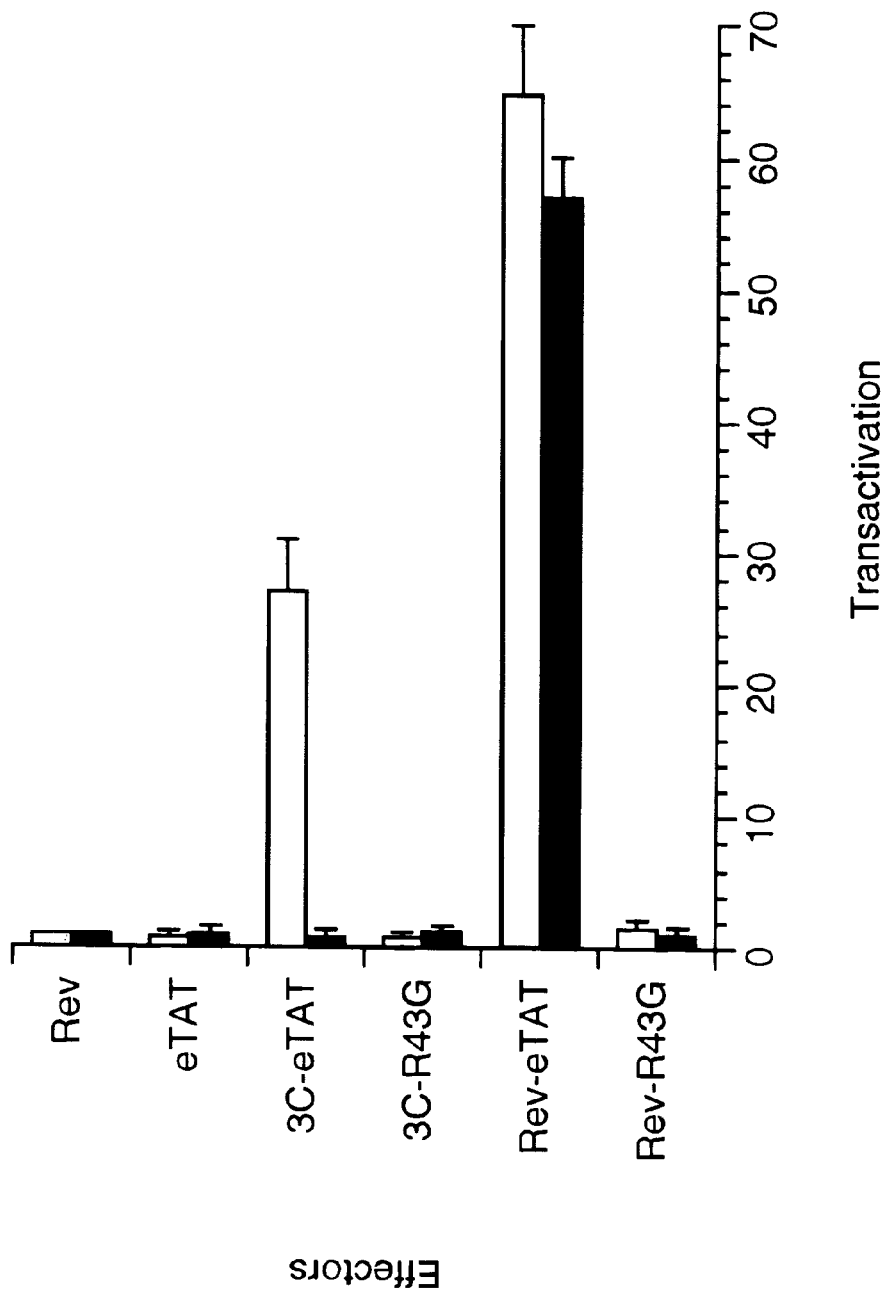

FIG. 2. Poliovirus 3C is sufficient to target the RNAs containing PV1 or PV2 stem-loop d sequences in vivo. HeLa cells were cotransfected with effector plasmids and either the pLTR/PV2/CAT (grey bars) or pLTR/ΔII/CAT (black bars) reporter plasmids. At~48 h after transfection, cells were harvested and induced CAT activities determined. Average CAT activities, derived from four separate experiments, are presented relative to that observed for Rev, which was arbitrarily set at 1 for each reporter. Error bars represent the observed standard deviation.

Figure 3:
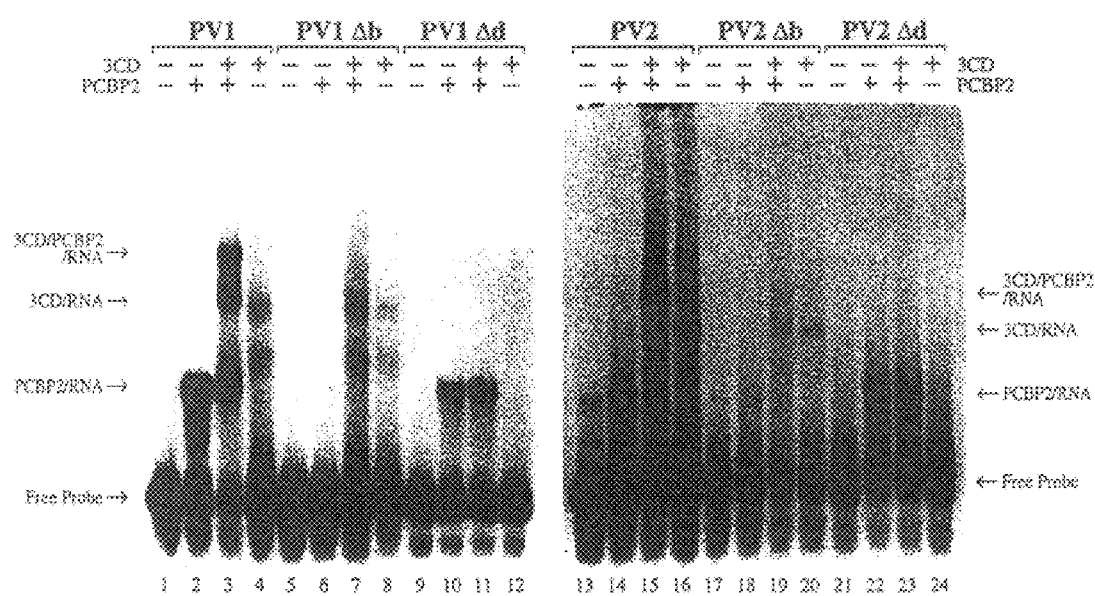

FIG. 3. Analysis of 3CD RNA binding in vitro. RNA electrophoretic mobility shift analysis with RNA probes derived from PV1 (lanes 1–12) or PV2 (lanes 13–24). The indicated RNA probes were incubated in binding buffer alone (lanes 1, 5, 9, 13, 17, and 21), with PCBP2 (lanes 2, 6, 10, 14, 18, and 22), with PCBP2 and PV1 3CD (lanes 3, 7, 11, 15, 19, and 23), or with 3CD alone (lanes 4, 8, 12, 16, 20, and 24). Specific RNA-protein complexes were separated from free probe by native gel electrophoresis and are indicated at the sides of the figure.

Figure 4A:
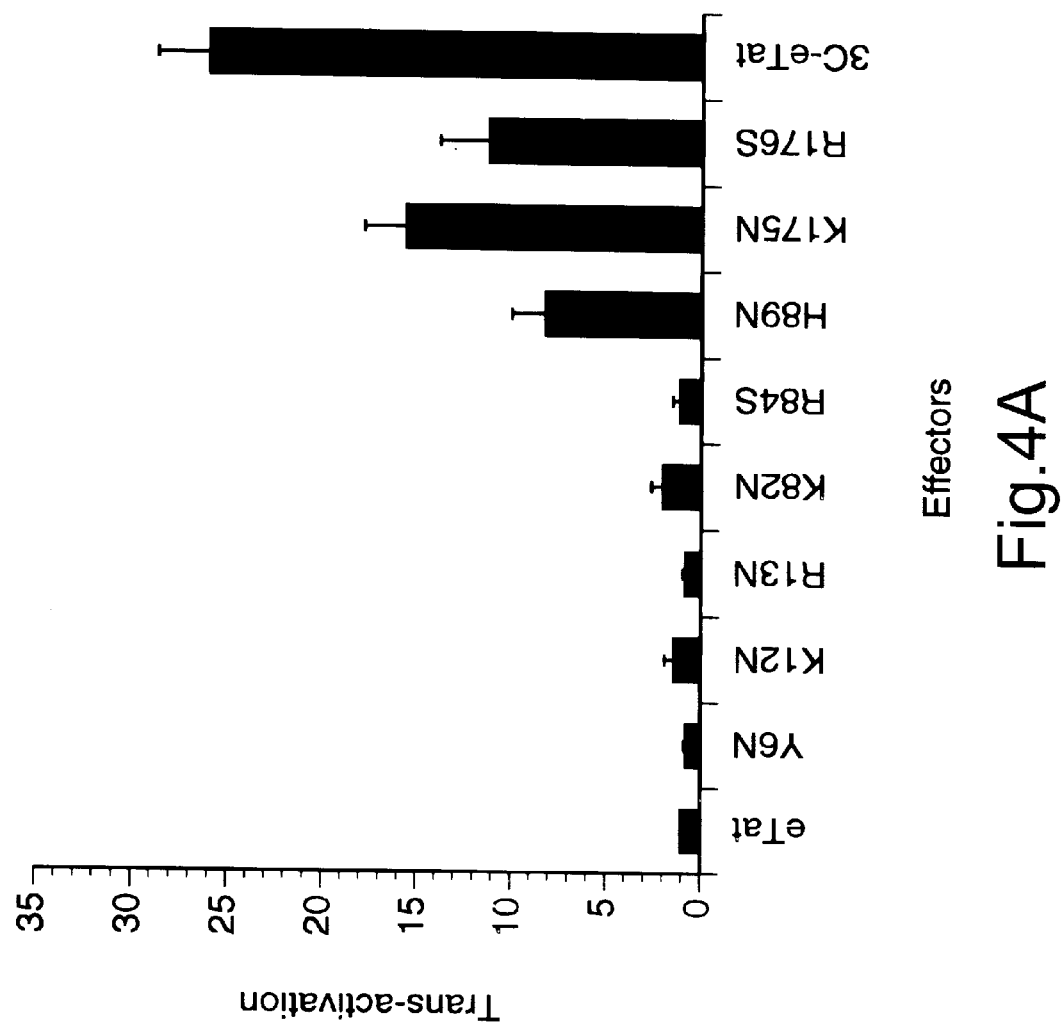
Figure 4B:
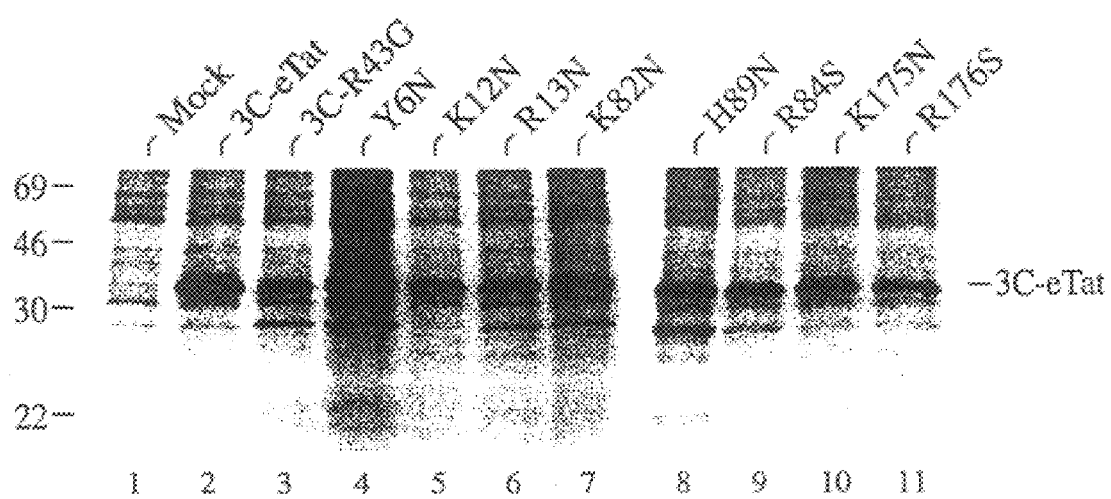
Figure 4C:
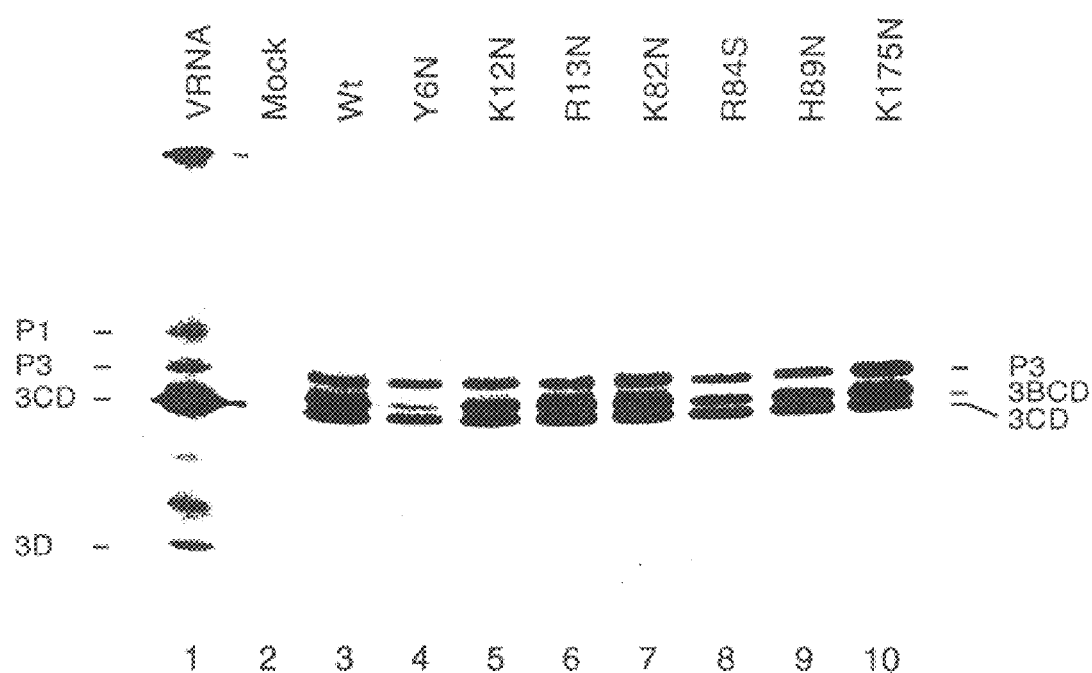

FIGS. 4A to 4C. RNA binding, expression, and proteolytic activity of mutant 3C proteinases. (FIG. 4A) HeLa cells were cotransfected with effector plasmids and the pLTR/PV2/CAT reporter. Induced CAT activities were measured from the extracts of transfected cells and are presented relative to that observed for eTat, which was arbitrarily set at one. (FIG. 4B) COS cells were either mock transfected (lane 1) or transfected with wild-type or mutant effector plasmids expressing 3C-eTat fusion proteins. Cells were metabolically labeled with [$^{35}$S]methionine at 40 h after transfection, and 3C-eTat proteins immunoprecipitated using antiserum directed against 3C. Numbers at left indicate the mobility of protein markers, in kilodaltons. (FIG. 4C) Analysis of the proteolytic activities of 3C proteinases containing single amino acid substitution mutations. In vitro synthesized RNAs derived from plasmids encoding the poliovirus P3 region containing single amino acid substitutions in 3C residues were translated in a HeLa cell extract in the presence of [$^{35}$S]methionine. The cleavage products resulting from endogenous 3C activity were then analyzed by SDS-polyacrylamide gel electrophoresis.

FIGS. 5A and 5B. FIG. 5A. Reporter construct suitable for use in a Tat:cDNA fusion assay. FIG. 5B. Effector constructs suitable for use in the Tat:cDNA fusion assay.

Figure 6:
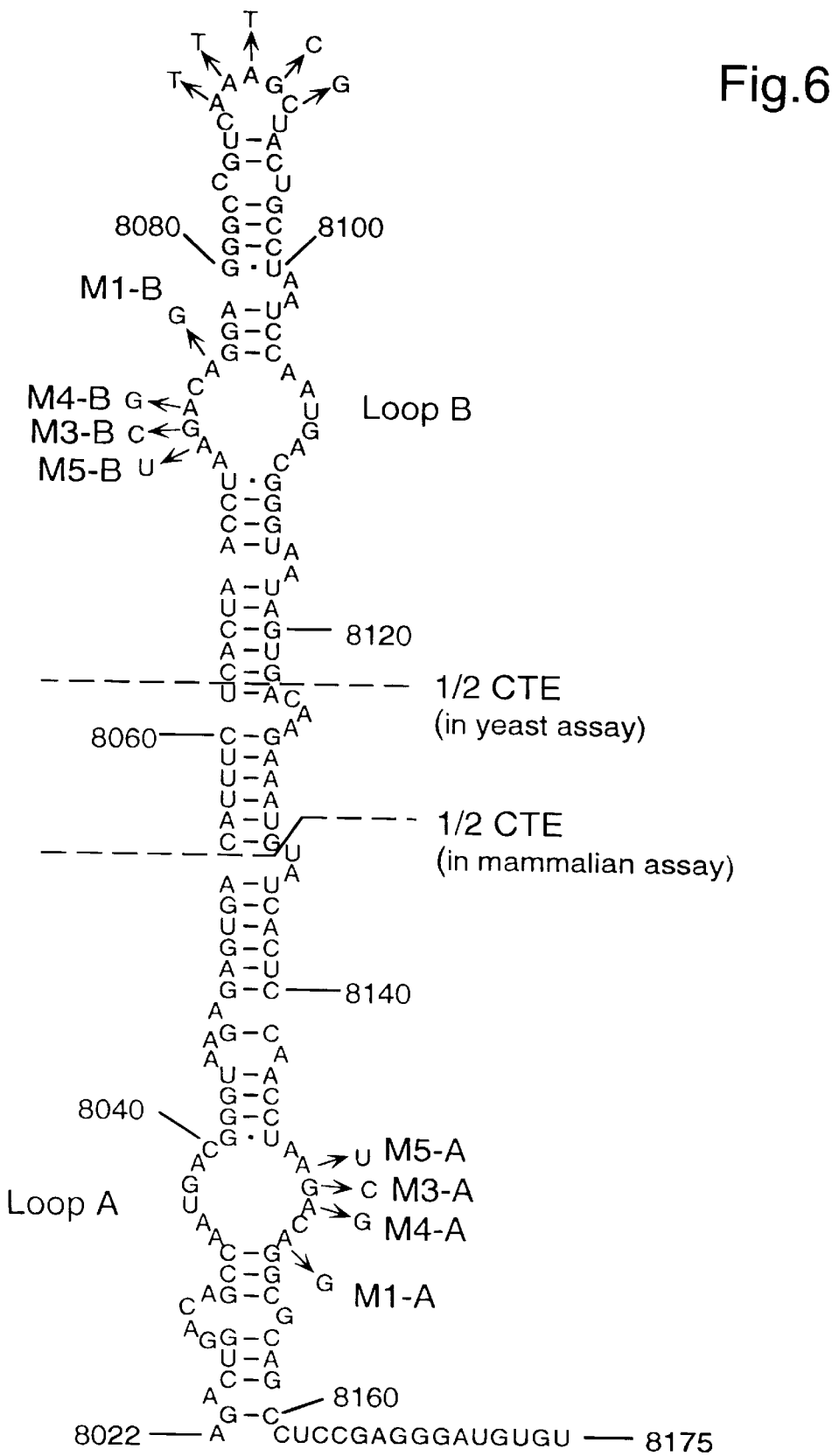

FIG. 6. Predicted structure of the MPMV CTE RNA element (SEQ ID NO:4). The CTE is believed to fold into a highly helical RNA structure that presents two identical RNA loops, designated loop A and loop B, that serve as specific protein binding sites. The full-length CTE used in this manuscript is the MPMV sequence indicated. The extent of the "½ CTE" RNA sequences used in the yeast and mammalian RNA:protein binding assays is also shown, as is the location of selected point mutants. Sequence coordinates refer to the sequence of the full-length MPMV genome and are as defined by Ernst et al, RNA 3:210–222 (1997).

Figure 7:
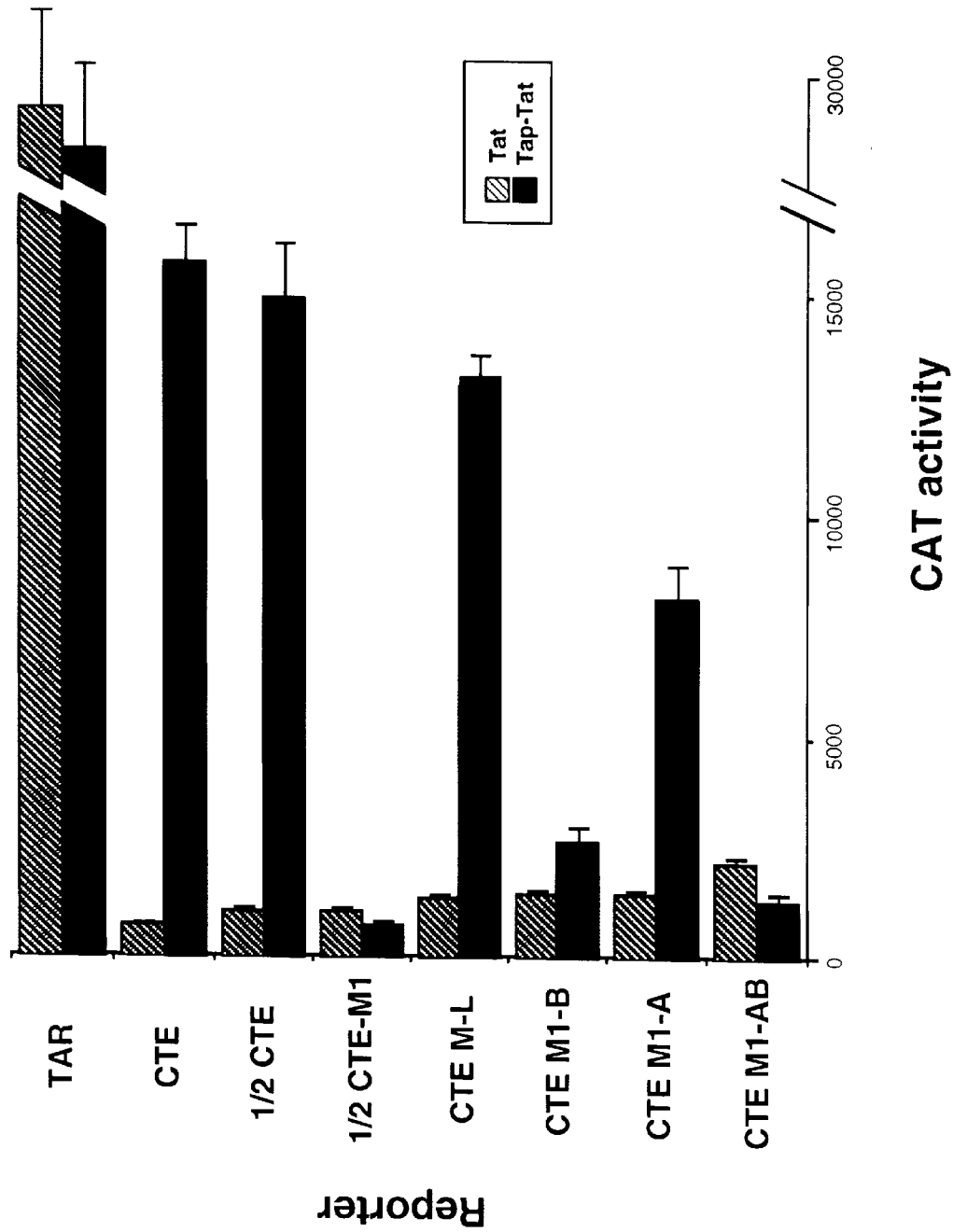

FIG. 7. Demonstration of specific binding by Tap to the CTE RNA target in human cells. The assay shown relies on the known ability of the HIV-1 Tat protein to activate transcription from the HIV-1 LTR when targeted to an RNA target sequence introduced in place of the viral TAR element (Blair et al, RNA 4:215–225 (1998). In this case, the TAR element has been replaced by the indicated wild-type or mutant forms of the MPMV CTE in an indicator construct in which expression of the cat indicator gene is controlled by the resultant chimeric HIV-1 LTR promoter. CAT activities observed in transfected human 293T cells, upon expression in trans of wild-type Tat or a Tat-Tap fusion protein, are indicated. Human 293T cells (35 mm culture) were transfected with 100 ng of the CAT-based indicator construct, 500 ng of the Tat or Tat-Tap expression plasmid, 1 μg of pBC12/CMV and 25 ng of the pBC12/CMV/β-gal internal control plasmid. Cells were harvested, and CAT and β-gal activities measured, at 48 hrs after transfection.

Figures 8A, 8B:
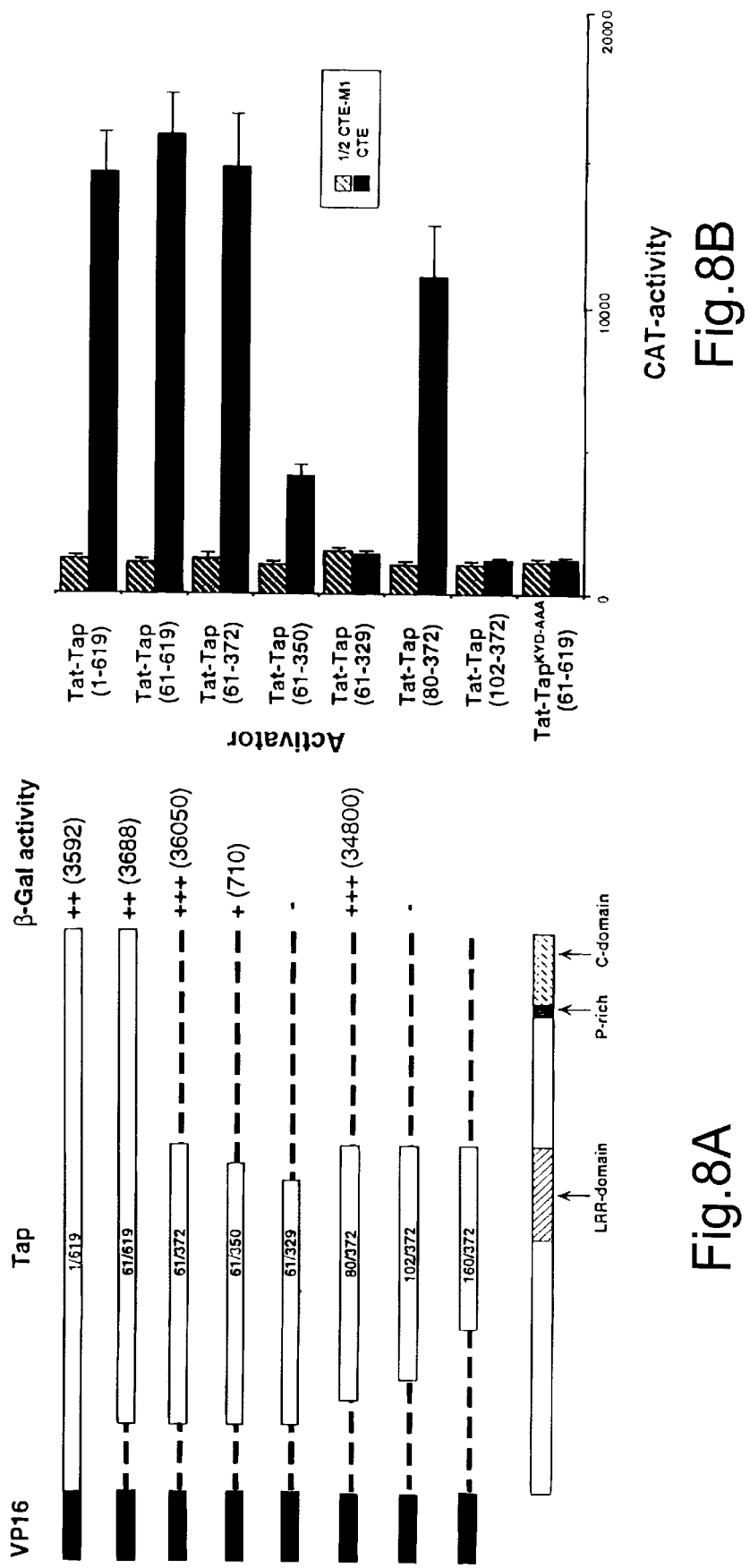

FIGS. 8A and 8B. Definition of the RNA binding domain of human Tap. (FIG. 8A) Schematic representation of deletion mutants of Tap, expressed in yeast in the form of VP16 transcription activation domain fusions, and their relative CTE RNA binding activity as measured in the yeast three hybrid assay, as described in Table 3. The observed average level of binding activity is given in relative terms and is also shown as absolute β-gal activity drawn from a representative experiment. The location of the leucine-rich-repeat (LRR), proline-rich (P) and C-terminal motifs of human Tap as given at the bottom and are as proposed by Segrefet et al, EMBO J. 16:3256–3271 (1997). +++, activity above wild-type; ++, activity comparable to wild-type; +, partial activity; –, no detectable activity. (FIG. 8B) The level of CTE RNA binding by the indicated Tap mutants was analyzed by transfection of human 293T cells, as described in FIG. 7. The various Tap proteins were expressed as fusions to the full-length HIV-1 Tat protein and their ability to bind the CTE then measured using an HIV-1 LTR based indicator construct bearing the CTE in place of TAR. All Tat-Tap fusion proteins proved equivalently active when tested on a wild-type HIV-1 LTR based indicator construct.

Figure 9A:
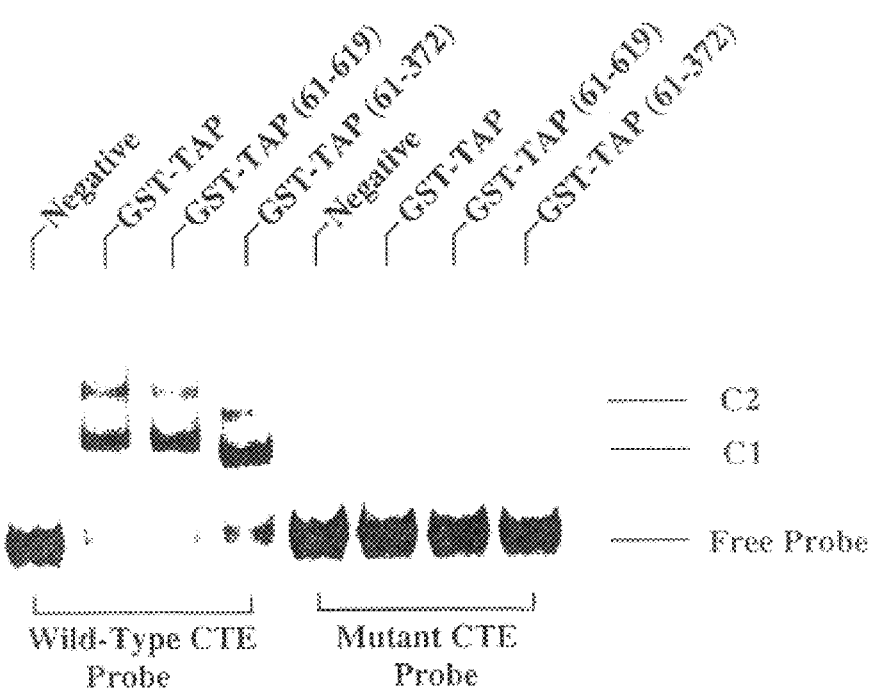
Figure 9B:
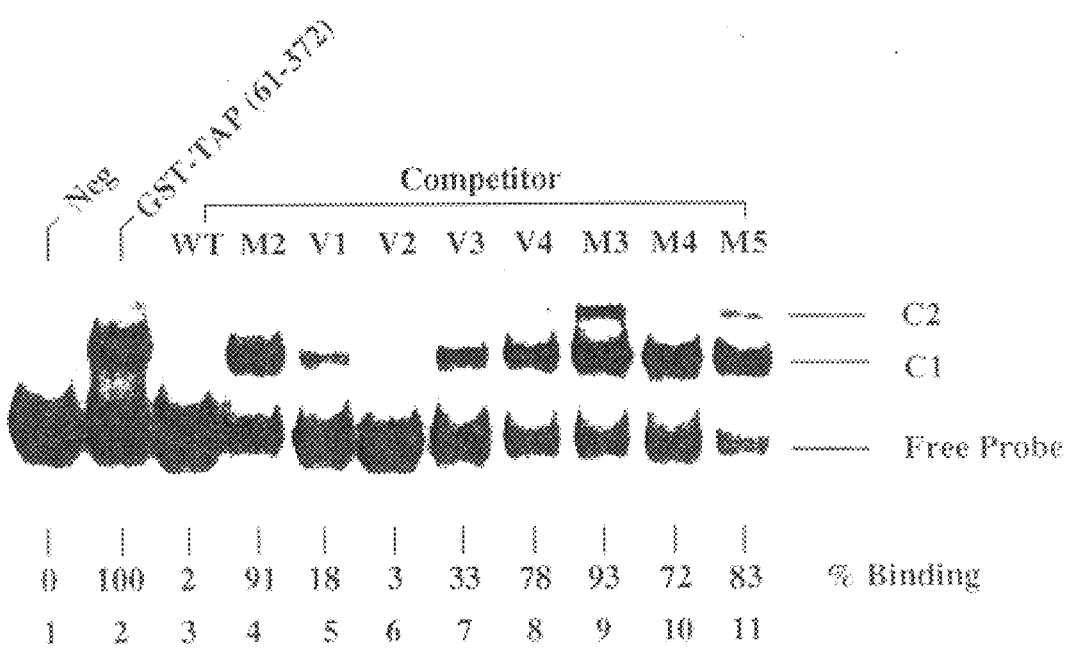

FIGS. 9A and 9B. Tap binds the CTE specifically in vitro. (FIG. 9A) GST-fusion proteins, consisting of GST linked to the indicated full-length or truncated forms of human Tap, were expressed in bacteria and then purified by affinity chromatography. A full-length wild-type or M2-AB mutant CTE probe was synthesized by in vitro transcription in the presence of $[\alpha\text{-}^{32}P]$CTP and $\sim10^4$ cpm (~0.1 ng) then mixed with ~25 ng of the GST-Tap fusion protein in a 20 μl reaction mix containing 5 μg of non-specific competitor RNA. After incubation at 4° C. for 20 min, the reaction products were resolved on a 5% native polyacrylamide gel and visualized by autoradiography. C1 and C2 refers to two distinct retarded complexes observed when using the full-length wild-type CTE probe. (FIG. 9B) Competitor RNAs, consisting of the indicated CTE mutations introduced into the full length CTE were synthesized in vitro and then added at an ~200 fold molar excess to the Tap:CTE binding reaction 10 min. prior to addition of the labeled CTE RNA probe. The relative level of binding was then quantitated by Phosphorimager and is given as percent residual binding, with binding in the absence of specific competitor set at 100%.

Figure 10:
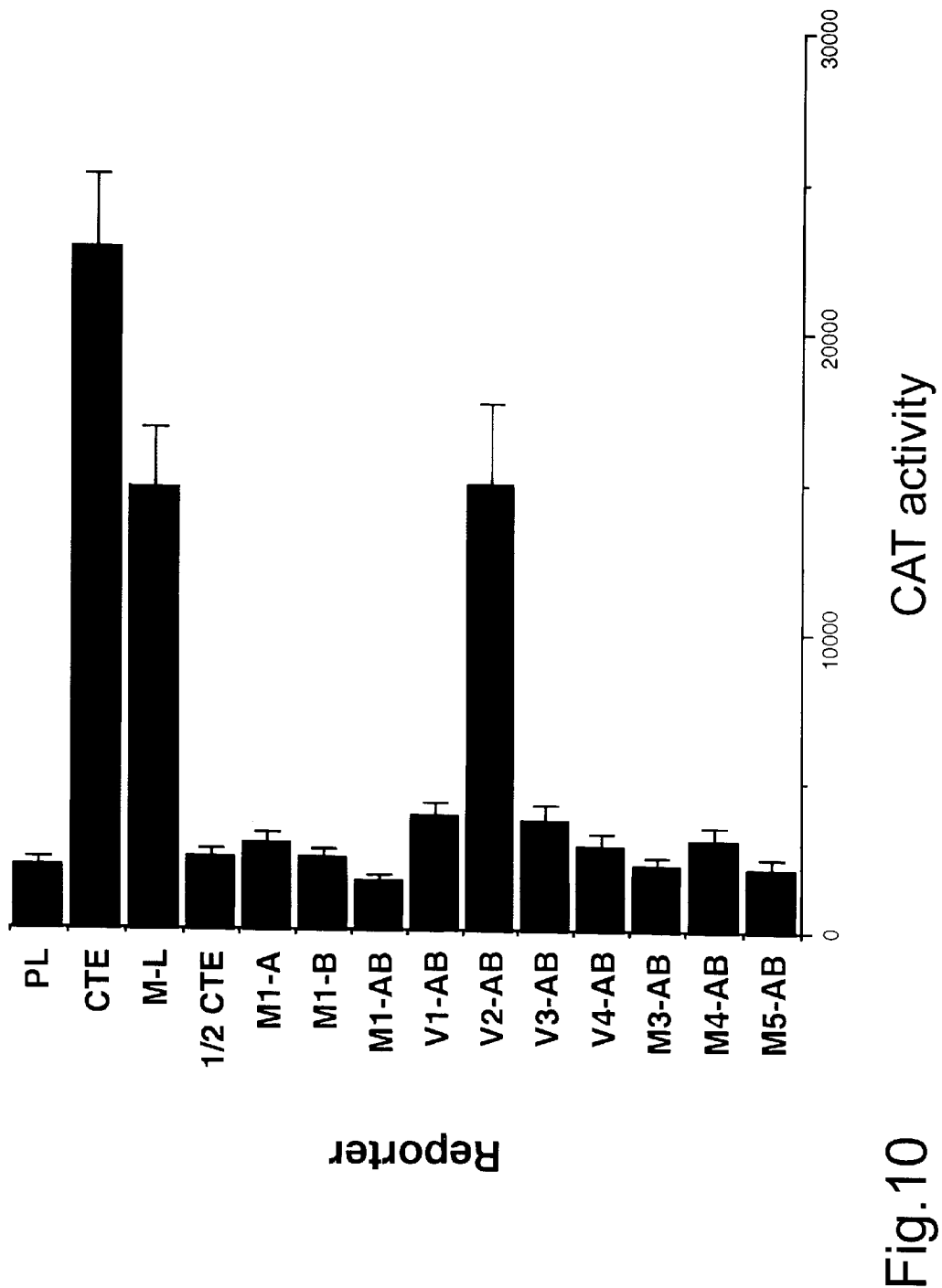

FIG. 10. RNA export activity of the indicated CTE variants in human cells. The pDM128/CTE indicator construct contains the cat gene and CTE located between 5' and 3' splice sites. CAT expression is therefore dependent on the nuclear export of an unspliced cat mRNA, a process that is inefficient in the absence of a functional cis-acting RNA export signal, such as the CTE. pDM128/CTE variants, containing the indicated CTE mutants, were analyzed in comparison to the wild-type CTE or to a form of DM128 (pDM128/PL) that contains a poly-linker in place of the CTE and that therefore serves as a negative control. Human 293T cells (35 mm culture) were transfected with 25 ng of the indicated pDM128 derivative, 25 ng of pBC12/CMV/β-gal and 1 μg of pBC12/CMV as a carrier. CAT and β-gal activity was determined at ~48 hrs after transfection.

Figure 11B:
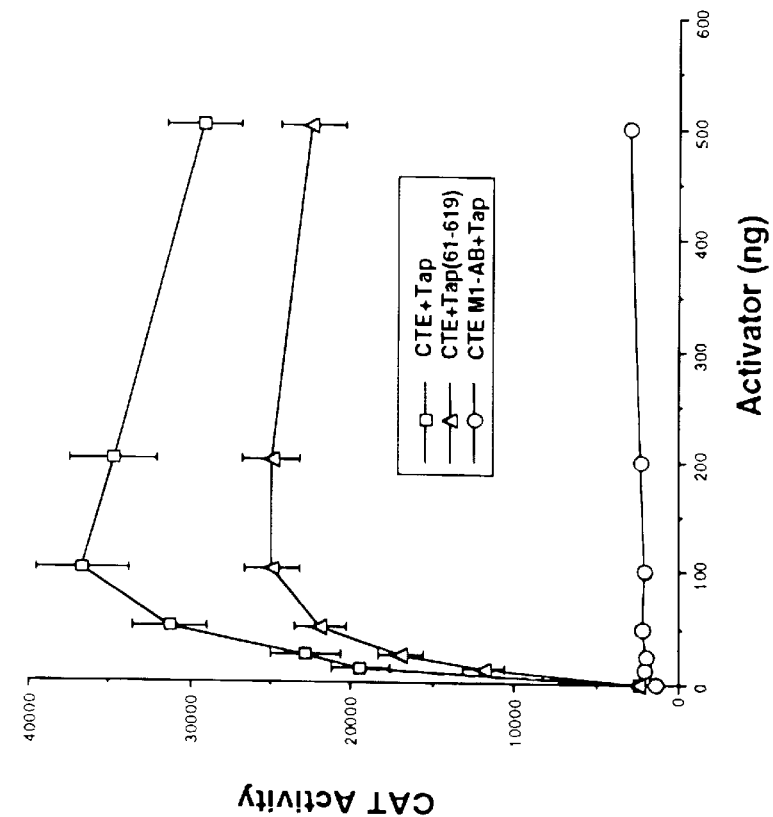
Figure 11A:
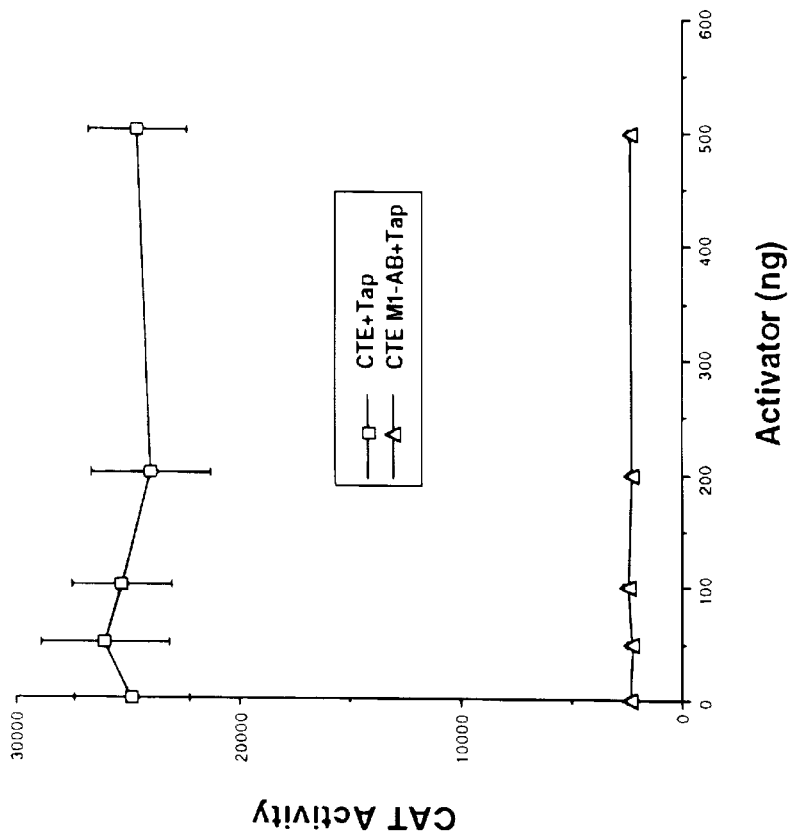
Figure 11C:
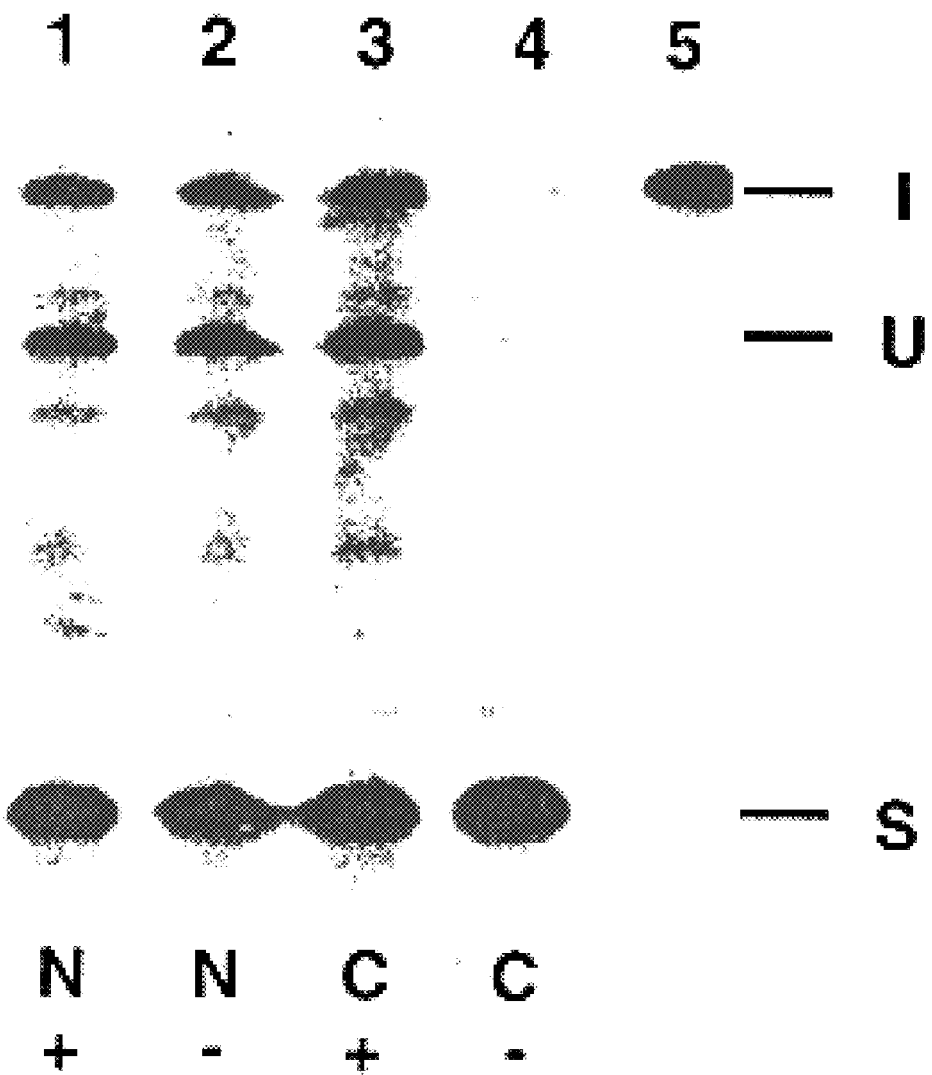

FIGS. 11A–C. Expression of human Tap induces CTE-dependent nuclear mRNA export in normally non-permissive quail cells. (FIG. 11A) Human cells, such as 293T cells, are highly permissive for MPMV CTE function and expressing increasing levels of human Tap does not enhance CTE activity appreciably. (FIG. 11B) The quail cell line QCl-3 does not normally support MPMV CTE function, as shown by the nearly equivalent level of activity observed with pDM128/CTE constructs containing wild-type or defective M1 mutant forms of the CTE. However, cotransfection of expression plasmids encoding the full-length or 61–619 form of human Tap effectively rescues indicator gene expression from the wild-type, but not mutant, CTE indicator plasmid. Human 293T cells (FIG. 11 A) or QCl-3 cells (FIG. 11B) were transfected with 25 ng of wild-type or M1 mutant forms of the pDM128/CTE indicator plasmid and increasing levels, up to 500 ng, of a pBC12/CMV based full-length or truncated Tap expression plasmid. Levels of transfected DNA were maintained at a constant level by addition of the parental pBC12/CMV plasmid. Cells were harvested at 48 hrs post-transfection and CAT activities determined as described. (FIG. 11C) Levels of expression of the spliced (S) or unspliced (U) RNA encoded by pDM128/CTE, in the nucleus (N) or cytoplasm (C ) of transfected QCl-3 cells, was determined using RNase protection analysis in cells transfected with pDM 128/CTE in the presence (+) or absence (–) of a cotransfected human Tap expression plasmid. QCl-3 cultures (six well 35 mm plates) were each transfected with 25 ng of pDM128/CMV, 100 ng of pcTap and 400 ng of pBC12/CMV. At 72 hrs after transfection, total nuclear and cytoplasmic RNA was harvested and levels of each RNA species determined. I, input probe; U, unspliced DM128 RNA; S, spliced DM128 RNA.

Figure 12B:
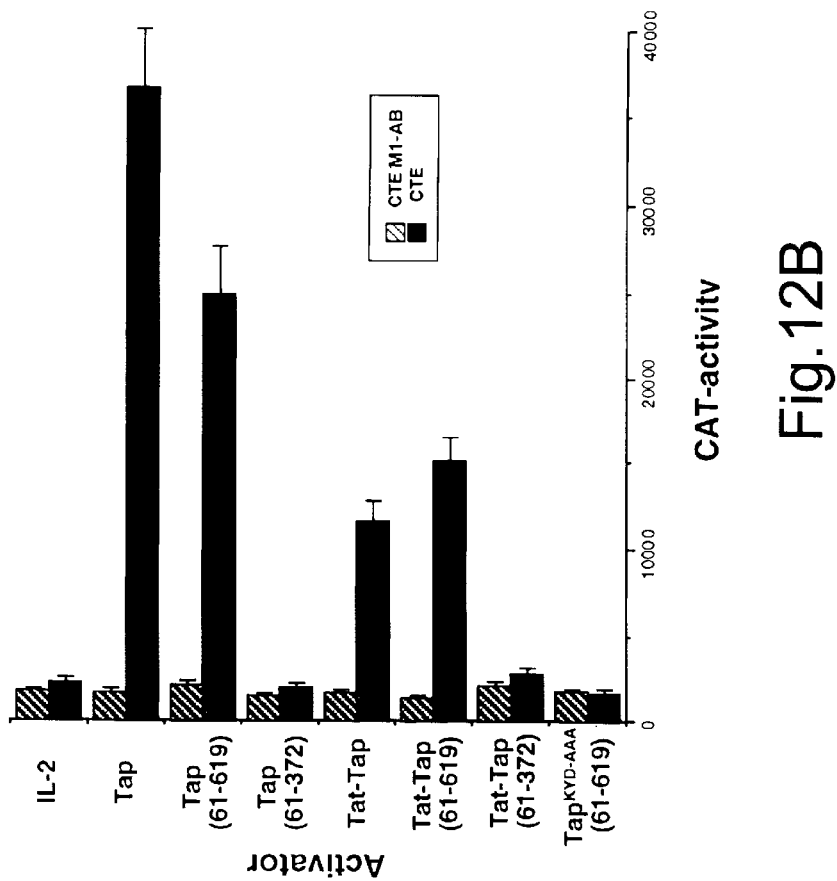
Figure 12A:
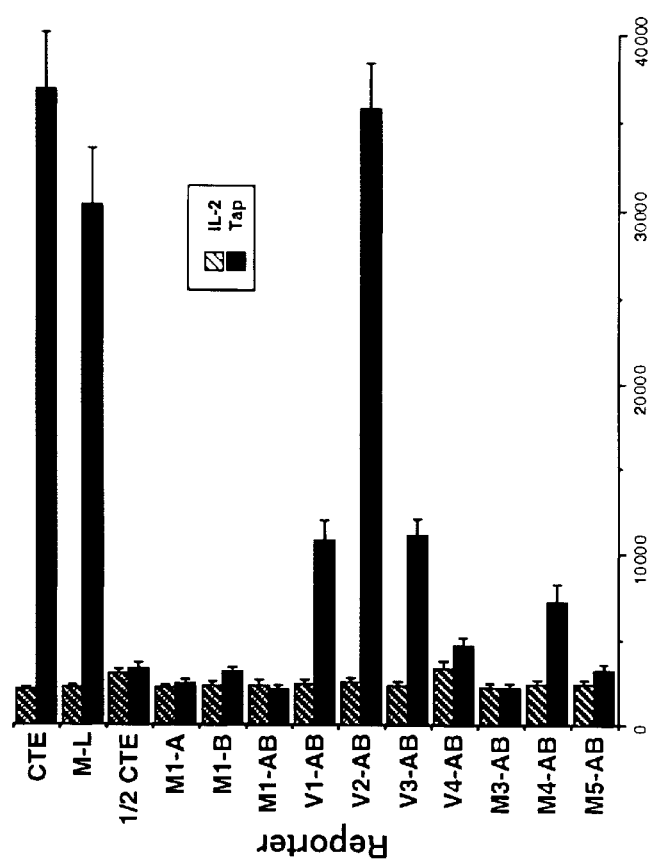

FIGS. 12A and 12B. Biological activity of CTE and Tap mutants in transfected QCl-3 cells. (FIG. 12A) Derivatives of the pDM128/CTE indicator plasmid, containing the indicated CTE mutations, were analyzed for biological activity in QCl-3 cells in the presence or absence of cotransfected human Tap. (FIG. 12B) The relative ability of the indicated mutant forms of Tap, expressed either unfused or fused to the HIY-1 Tat protein, to activate cat expression from the pDM128/CTE indicator construct in QCl-3 cells, is indicated.

DETAILED DESCRIPTION OF THE INVENTION

The present invention provides a method and kit for detecting RNA:protein interactions in vivo. The method depends on the transcriptional activation of a promoter, for example, the human immunodeficency virus type 1 (HIV-1) long terminal repeat (LTR) promoter, by a RNA-targeted lentiviral Tat protein.

Normally, HIV-1 Tat is recruited to the HIV-1 LTR promoter through an interaction with an RNA stem-loop structure designated TAR, resulting in enhanced transcription and elongation, as well as initiation (Cullen, Cell 73:417–420 (1993)). It has been shown that Tat can also be targeted to the HIV-1 LTR promoter by certain heterologous RNA binding domains. Replacement of TAR sequences in the HIV-1 LTR with RNA targets for HIV-1 Rev or the coat protein of bacteriophage MS2 (MS2CP), results in promoters responsive to a Tat-Rev or a MS2CP-Tat fusion protein, respectively, but not to Tat itself (Selby et al, Cell 62:769–776 (1990); Southgate et al, Genes & Dev. 5:2496–2507 (1991); Tiley et al, Genes & Dev. 6:2077–2087 (1992)). The present invention results, at least in part, from the realization that the ability to target Tat to the HIV-1 LTR promoter by heterologous RNA binding domains provides basis for a generalized method for detecting RNA:protein interactions using, for example, automatable tissue culture assays or FACS analysis.

In accordance with the method of the present invention, a reporter construct and an effector construct are provided, as is a host cell transformed therewith. The reporter construct comprises a Tat-responsive promoter operably linked to a heterologous 3' RNA binding site, which RNA binding site is operably linked to a 3' indicator gene. The Tat-responsive promoter can be a cellular or viral derived promoter. For example, the promoter can be derived from a lentivirus LTR, such as the HIV-1, HIV-2, simian immunodeficiency virus (SIV), equine infectious anemia virus (EIAV) or bovine immunodeficiency virus (BIV) LTR. Advantageously, the reporter construct includes a minimum Tat-responsive LTR promoter, e.g., the NF-κB, SP1 binding site and TATA box of the U3 region of the HIV-1 LTR. To avoid potential inhibition of translation of the indicator gene by the RNA binding site, an internal ribosome entry site (IRES) can be inserted 3' to the heterologous RNA binding site and 5' to the indicator gene sequence and in operable linkage therewith.

In the Examples set forth below, specific reporter constructs are described. In Examples 1–4, for instance, reporter constructs comprising the RNA stem-loop binding (i.e., target) site for polio- and rhino-viral 3C proteins are described. Depending on the RNA:protein interaction to be assessed, other RNA binding sites can be selected for inclusion in the reporter construct. Examples of such heterologous RNA binding sites include those from any of a variety of pathogenic RNA viruses, such as picornaviruses, including hepatitis A virus, human T-cell leukemia virus, comoviruses, paramyxoviruses, filoviruses, including Marburg and ebola viruses, influenza, hepatitis C and bunyaviruses, including rift valley fever virus. Further examples include cellular RNA binding sites, for example, RNA targets that modulate splicing patterns of cellular genes. Certain such sequences are activated during cancer and modulate the expression pattern of oncogenic gene products thereby rendering them more oncogenic.

Indicator genes suitable for use in the reporter constructs of the invention can be selected from any of a variety of genes encoding a readily detectable protein product. Examples of indicator genes include the chloramphenicol acetyl transferase (CAT), luciferase, green fluorescent protein (GFP) secreted alkaline phosphatase (SEAP) and P-galactosidase genes. The indicator gene can also encode a cell surface marker such as Thy 1, CD4 or CD8.

To ensure efficient translation, an IRES can be positioned in the reporter construct 5' to the indicator gene. The IRES can be derived from either a viral or cellular gene that undergoes cap-independent translation. Preferably, the IRES is derived from a picornavirus, such as polio virus or encephalomyocarditis virus.

The reporter construct can be present in a vector, such as a plasmid, or a virus, such as a retrovirus.

The effector construct of the invention comprises a sequence encoding a fusion protein comprising a Tat protein activation domain and the protein cognate of the RNA binding site present in the reporter construct (that is, "the RNA binding moiety"). The fusion protein encoding sequence can be present in the effector construct operably linked to a promoter functional in the host cell to be used. Suitable promoters include cytomegalovirus intermediate early promoter, the SV40 early promoter or a retroviral LTR promoter. In addition, the effector construct can include a functional poly-A addition site derived, for example, from a virus such as SV40, or from a cellular gene, such as the human β-globin or rat preproinsulin gene.

The constructs of the invention can be introduced into host cells, preferably, vertebrate host cells, more preferably mammalian host cells, most preferably, human host cells. Suitable host cells include human fibroblast cell lines (e.g., HeLa cells, 293T cells, 293 cells, W238 cells and HOS cells), rodent cell lines (e.g., 3T3 cells, L cells, C127 cells and BHK cells), human T-cells (e.g., Jurkat, CEM and H9 cells), and monkey cell lines (e.g., CV1 cells and COS cells). The constructs can be introduced using any of a variety of techniques and agents, including electroporation, calcium phosphate precipitation, DEAE-dextran, lipofectin, cationic lipids and viral (e.g., retroviral) infection.

In one embodiment of the present invention, the above-described reporter and effector constructs are introduced into a host cell and the cell is cultured under conditions such that the fusion protein encoded in the effector construct is produced and interacts with the RNA binding site of the reporter construct (that is, via the binding of the RNA binding moiety of the fusion protein with the RNA binding site). The interaction of the fusion protein with the RNA binding site results in expression of the indicator gene and thereby production of the indicator protein, which can be detected using suitable means. In accordance with this embodiment, the effect of alterations in the RNA binding moiety of the fusion protein can be determined by comparing the level of indicator protein produced in the presence and absence of the alteration. Alterations that enhance interaction of the RNA binding moiety with the RNA binding site can be expected to increase the level of indicator protein produced, visa versa for alterations that diminish that interaction. The effect of alterations in the RNA binding site can examined using a similar approach.

The above-described host cells can also be used to screen test compounds for their ability to modulate the RNA:protein interaction necessary to effect expression of the indicator gene and thereby production of the indicator protein. In such screens, host cells comprising the reporter and effector constructs are contacted with the test compound, the cells are cultured and the level of expression of the indicator gene is determined (e.g., by determining the level of production of the indicator gene product). A decrease in the expression of the indicator gene in the presence of the test compound can be expected to be indicative of a compound that inhibits interaction of the RNA binding moiety of the fusion protein with the cognate RNA binding site (visa versa an increase in expression). Compounds selected in accordance with the above screen can be expected to have therapeutic potential. For example, compounds that inhibit binding of a viral RNA binding protein to its cognate RNA binding site gene can be expected to have potential as antiviral therapeutic agents. Compounds that inhibit cellular RNA:protein interactions that modulate expression patterns of oncogenic gene products and, for example, thereby render them more oncogenic, can be useful in treating or preventing neoplasia.

In another embodiment, the present invention relates to a method of screening a Tat:cDNA fusion library for genes that encode proteins able to activate the Tat-responsive promoter linked indicator gene and thus proteins that can be expected to have a RNA binding moiety that interacts with the RNA binding site of the reporter construct used. To identify a protein specific for a particular RNA target (binding site) sequence, a reporter construct comprising the following, proceeding from 5' to 3', can be used: i) a minimum Tat-responsive promoter (e.g., the HIV-1 LTR U3 region promoter), ii) a polylinker, or unique restriction enzyme site, that permits insertion of a sequence encoding the RNA target of interest (Tat works well when its RNA target is close to the LTR, accordingly it is preferably that this be a minimal RNA target); iii) a control RNA stem-loop target sequence (e.g., the RRE stem-loop II target for Rev or the cloverleaf stem-loop target for poliovirus 3C) advantageously inserted immediately 3' to the RNA target sequence (this serves as a control to: (a) show the construct is flnctional, and (b) identify transfected cells that can be activated by Tat fusion proteins); iv) optionally an IRES, and v) an indicator gene (e.g., one suitable for use in a FACS analysis—preferably, GFP or, alternatively, a cell surface marker (e.g.: Thy 1, CD4 or CD8). After insertion of the RNA target encoding sequence, the reporter construct is introduced into a cell line, e.g. HeLa cells, using transfection or transduction, advantageously, with a selectable marker gene such as hgr$^R$ or G418$^R$. Individual colonies of the transformants can then be cloned and a colony that responds to Tat fusion proteins identified by transfecting or transducing a sample of each colony with a construct expressing, for example, a Tat-Rev fusion protein (if the reporter constructs contains RRE stem-loop II) or a 3C-eTat fusion (if the reporter construct contains the poliovirus RNA cloverleaf). A highly responsive clone can be identified by FACS analysis for, for example, GFP expression. Once a maximally reactive clone is identified, the screen can be carried out. For this purpose, an oligo dT primed, directional cDNA library can be prepared using mRNA from cells predicted to express the protein specific for the RNA target sequence. These cDNAs can be cloned into an effector construct, for example, at a site located at the 3' end of the Tat open reading frame. Although about two-thirds of the inserted cDNAs may be out of translational reading frame with Tat, one-third will be in frame and will, upon translation, yield fusion proteins consisting of Tat linked to a library of cellular proteins, including proteins specific for the RNA target sequence (it will be appreciated that the RNA target specific protein (that is, the RNA binding moiety of the fusion protein) can also be present in the fusion protein 5' to Tat by appropriate design of the effector construct. At least two possible effector fusion expression approaches can be used. In one case, the fusions proteins can simply be expressed using an expression plasmid. In a preferred method, however, the effector construct is present in a transduction vector (e.g. a murine leukemia virus retroviral transduction vector). In either case, the fusion protein expression library (consisting of, for example, ≧10$^7$ individual clones) can be introduced into cultures of the clone derived above by either transfection or, alternatively, transduction after packaging (e.g., in a high efficiency amphotropic retroviral packaging cell line. The cells can then be analyzed, for example, by FACS, for expression of the indicator gene product and positive cells sorted out or otherwise selected. Sequences encoding the RNA binding moiety of the fusion protein present in the selected cells can be recovered, for example, by polymerase chain reaction using primers specific for the vector backbone, and the encoded protein can be analyzed in vitro and in vivo for its ability to specifically interact with the relevant RNA target sequence. The identification of a protein that binds to a particular RNA binding site provides insight into cellular processes and makes possible the identification of compounds that can be used to modulate that interaction, using the compound screen described above.

In another embodiment, the present invention relates to a kit comprising a construct of the invention, for example, disposed within a container means. The kit can comprise either the reporter or effector construct, or both. In the context of the kit, the reporter construct can include a sequence encoding the RNA binding site or merely a site that permits insertion of such an encoding sequence. Likewise, an effector construct of the present kit can include a sequence encoding a protein comprising an RNA binding moiety or merely a site for insertion of such an encoding sequence. The construct(s) can be in dry form or in solution. The construct(s) can be present in the kit in isolation or as an insert in a vector. Further, the construct(s) can be present in a host cell. The kit can be designed so as to facilitate the practicing of the present methods. In that regard, the kit can include suitable control constructs, such as an effector construct comprising a sequence encoding a Tat-Rev or eTat-3c fusion protein.

Certain aspects of the invention are described in greater detail in the non-limiting Examples that follow.

EXAMPLES

The following experimental details relate to the Examples 1–4 that follow.

Plasmid Construction

The reporter plasmid pLTR/PV2/CAT was previously described as pSLIIB/CAT (Tiley et al, Genes & Dev. 6:2077–2087 (1992)). pLTR/ΔII/CAT was constructed by polymerase chain reaction (PCR) amplification of PV2/CAT sequences, using an oligonucleotide primer containing a Hind III restriction endonuclease cleavage site that anneals to nucleotides 109–140 of PV2 and an oligonucleotide primer that anneals to 3' CAT sequences. The amplified products were then cleaved with restriction endonucleases Hind III and Nco I and ligated to pLTR/PV2/CAT digested with the same enzymes. The pLTR/PV2Δb/CAT and pLTR/PV2Δd/CAT reporters were constructed by recombinant PCR using oligonucleotide primers that correspond to PV2 nucleotide sequences 7–40 encoding a GTACCC to AAGCTT (nt 20–25) substitution mutation or oligonucleotide primers that correspond to PV2 sequences 48–86 encoding a four nucleotide deletion mutation (nt 67–70), respectively, and flanking oligonucleotide primers. The resulting recombinant PCR products were digested with Hind III and Nco I and introduced into pLTR/PV2/CAT digested with the same enzymes. The pLTR/PV1/CAT and pLTR/HRV14/CAT reporters were derived from pLTR/PV2/CAT by recombinant PCR using standard techniques.

The plasmids expressing Rev (pcRev), eTat (peTat), and Rev-eTat (pcRev-eTat) have been previously described (Madore et al, J. Virol. 67:3703–3711 (1993)). The p3C-eTAT and pRV3C-eTAT effector plasmids were constructed by PCR amplification of PV1 3C or HRV14 3C sequences, respectively, using oligonucleotide primers containing unique Nco I or Sac I restriction endonuclease sites. The amplified products were then digested with Nco I and Sac I and introduced into pcRev-eTat (digested with the same enzymes) in place of Rev sequences. The pRev-R43G and p3C-R43G effectors were constructed by PCR amplification of eTat sequences encoding the R43G mutation from pR43G (Madore et al, J. Virol. 67:3703–3711 (1993)) using oligonucleotide primers containing unique Sac I or Xho I restriction sites. The amplified products were digested with Sac I and Xho I and ligated to either pcRev-eTat or p3C-eTat (digested with the same enzymes) in place of eTat sequences. Eukaryotic 3C-eTat expression plasmids encoding mutations in 3C sequences were constructed by recombinant PCR using oligonucleotides containing the described mutations. The pBC12/CMV/β-GAL control plasmid has been previously described (Fridell et al, Virology 209:347–357 (1995)).

The in vitro transcription/translation vector pT7-P3 contains the poliovirus type-I P3 region preceded by the poliovirus 5' NCR as well as the bacteriophage T7 promoter. Mutations were introduced into the 3C sequences within pT7-P3 by QuickChange site-directed mutagenesis (Stratagene). The plasmid, pT7-5' NCR, which contains PV1 sequences 1 to 747, has been described previously (Haller et al, J. Virol. 66:5075–5086 (1992)), as have PV1 based plasmids encoding RNA containing the Δb(pT7-PV1-S1) and Δd(pT7–5'Δd) mutations (Parsley et al, RNA 3:1124–1134 (1997)). Plasmids pT7-PV2, pT7-PV2Δb and pT7-PV2Δd were constructed by PCR amplification of wild-type PV2 sequences (1 to 108), PV2 sequences containing the Δb mutation, or PV2 sequences containing the Δd mutations with oligonucleotide primers that contain unique EcoR I and BamH I restriction sites. The amplified products were digested with EcoR I and BamH I and ligated to pGEM-3fZ (Promega) digested with the same enzymes.

Transfection and Analysis

HeLa cells were transfected by electroporation as described previously (Pendergrast et al, J. Virol 71:910–917 (1997)). Briefly, cells were mixed with ~20 μg of plasmid DNA in 0.25 mls of serum-free medium. The mixture was then transferred to a Gene Pulser cuvette (0.4 cm-wide electrode gap; Bio-Rad) and electroporated with a pulse of 260 V and 960 μFD in the Bio-Rad Gene Pulser. Cells were then transferred to a 10-cm dish containing rich medium. Similarly, 293 T cells were transfected using the calcium phosphate procedure (Cullen, Methods Enzymol. 152:684–704 (1987)). Approximately 48 h following transfection, cells were harvested and CAT activity was measured from extracts of transfected cell as previously described (Tiley et al, Genes & Dev. 6:2077–2087 (1992)). All transfections and subsequent analyses were performed at least three times to ensure reproducibility. When cell extracts were assayed for β-gal activity from the internal control plasmid, pBC12/CMV/β-GAL, transfection efficiencies were shown to be equivalent.

COS cells were transfected by the DEAE-dextran procedure (Cullen, Methods Enzymol. 152:684–704 (1987)) with plasmids expressing 3C-eTat fusions. At 40 h after transfection, cells were labeled with [$^{35}$S]methionine, and 3C containing proteins were immunoprecipitated from extracts of transfected cells with a rabbit polyclonal antiserum directed against 3C. Immune complexes were analyzed on SDS-polyacrylamide gels and visualized by autoradiography.

RNA Electrophoretic Mobility Shift Analysis

To generate RNA probes, the PV1 based plasmids (pT7-5' NCR, pT7-PV1-S1, pT7–5'Δd) were each digested with Dde I, while pT7-PV2, pT7-PV2Δb, and pT7-PVΔd were digested with Hind II, and the linearized templates were transcribed with bacteriophage T7 polymerase in vitro as described previously (Blair et al, Virology 218:1–13 (1996)). The $^{32}$P-labeled RNA probes were then gel purified and quantitated based on specific activity. RNA electrophoretic mobility shift analysis was performed as described previously (Blair et al, Virology 218:1–13 (1996)). Briefly, purified recombinant PCBP2 (125 nM) and/or purified recombinant 3CD (350 nM) proteins were incubated with $^{32}$P-labeled RNA probes and RNA/protein complexes were resolved by native polyacrylamide gel electrophoresis.

Analysis of 3C Proteolytic Activity

Wild-type pT7-P3 or pT7-P3 encoding mutations in 3C sequences were linearized with Aat II, and the linearized plasmids were transcribed by bacteriophage T7 polymerase in vitro. The resulting RNAs were then translated in vitro using a HeLa cell extract in the presence of [$^{35}$S]methionine (Todd et al, Virology 229:90–97 (1997)). The $^{35}$S-labeled 3C cleavage products were then analyzed by SDS-polyacrylamide gel electrophoresis followed by autoradiography.

EXAMPLE 1

Poliovirus 3C is Able to Target the Poliovirus 5' NCR in Mammalian Cells

To analyze the in vivo interaction of picomavirus 3C proteinases with their cognate RNA target sites, the reporter plasmid pLTR/PV2/CAT was constructed (FIG. 1B), in which the CAT indicator gene is positioned 3' to sequences (nt 1–750) corresponding to the poliovirus 5' NCR. The IRES present in this 5' NCR ensures the efficient translation of mRNAs transcribed from this reporter plasmid in mammalian cells. Expression of the linked indicator gene is controlled by a previously described (Tiley et al, Genes & Dev. 6:2077–2087 (1992)) HIV-1 LTR promoter derivative that contains RNA target sequences for the HIV-1 Rev protein in place of TAR (FIG. 1B). Therefore, all reporter constructs are responsive to a Rev-eTat fusion protein, which serves as a positive control for RNA targeted transcriptional activation throughout the analysis, but are not responsive to Tat alone. The pLTR/ΔII/CAT reporter plasmid is similar to pLTR/PV2/CAT except that it lacks the first 109 nt of the poliovirus 5' NCR, including all of the proposed RNA stem-loop structure shown in FIG. 1A. The pLTR/PV2/CAT or pLTR/ΔII/CAT reporter constructs were transfected into HeLa cells along with effector plasmids encoding HIV-1 Rev, the eTat protein, or various Rev-eTat or PV1 3C-eTat fusion proteins. Induced CAT activities were then determined at ~48 h after transfection.

As predicted, neither Rev nor eTat proved able to induce significant levels of CAT activity from either the pLTR/PV2/CAT or the pLTR/ΔII/CAT reporter plasmid (FIG. 2). In contrast, the 3C-eTat and Rev-eTat fusions induced levels of CAT activity from the pLTR/PV2/CAT reporter that were about 28-fold and about 64-fold greater, respectively, than observed with Rev alone (FIG. 2). In contrast, while the pLTR/ΔII/CAT reporter plasmid remained fully responsive to activation by Rev-eTat, it was entirely non-responsive to the 3C-eTat fusion protein. Therefore, activation of the pLTR/PV2/CAT reporter by 3C eTat is clearly dependent on the presence of poliovirus sequences that encode the RNA stem-loop structure shown in FIG. 1A. As expected, trans-activation of the pLTR/PV2/CAT reporter by Rev-eTat and 3C-eTat was dependent on the biological activity of the eTat protein in that fusion proteins containing a single amino acid mutation (Arg to Gly) at position 43 of eTat (R43G), previously shown to eliminate eTat activation domain function (Madore et al, J. Virol. 67:3703–3711 (1993)), were inactive (FIG. 2). Western analysis and immunoprecipitation analysis both showed that the various eTat fusion proteins were expressed at readily detectable levels in mammalian cells (see below). Overall, these data strongly suggest that the 3C-eTat mediated activation of the HIV-1 LTR promoter present in pLTR/PV2/CAT results from the recruitment of a functional eTat protein to the LTR promoter as a result of the interaction of 3C with its cognate RNA target.

In preliminary experiments, it was possible to detect activation of the pLTR/PV2/CAT reporter constructs by 3CD-eTat fusion proteins. This could result from protein instability or from a block in the accessibility of eTat to the HIV-1 LTR promoter upon fusion of the large 3CD protein (72 kDa) to eTat. At present, the question of whether 3CD exhibits a significantly higher affinity than 3C for poliovirus RNA in vivo has not been addressed It should also be noted that all 3C-eTat fusions encode a Cys to Ala amino acid substitution mutation in the proteolytic active site of 3C, a mutation that is necessary for high level expression of 3C-eTat in mammalian cells.

EXAMPLE 2

3C RNA Targeting Requires Specific Sequences in the Polioviruses Type 2 5'NCR To more completely address the RNA sequence specificity of the 3C/PV2 RNA interaction detected in FIG. 2, we constructed two mutant forms of the pLTR/PV2/CAT reporter plasmid were constructed. The pLTR/PV2Δb/CAT reporter contains a six nucleotide substitution (GUACCC to AAGCUU) at positions 20–25 of the PV2 genomic RNA. Nucleotides 20–25 map to stem-loop b of the RNA cloverleaf (FIG. 1A) and are required for the binding of the p36 cellular cofactor in vitro (Parsley et al, RNA 3:1124–1134 (1997), and see below).

The pLTR/PV2Δd/CAT reporter lacks four nucleotides (nt 67–70) that map to stem-loop d of the PV2 RNA cloverleaf (FIG. 1A). Deletion of nucleotides 67–70 of poliovirus RNA disrupts the interaction of 3CD with the RNA cloverleaf in vitro (Parsley et al, RNA 3:1124–1134 (1997)), and see below). Each reporter was cotransfected into 293T cells along with a Rev expression plasmid or an expression plasmid encoding one of the various Rev-eTat or 3C-eTat fusions, and CAT activities were measured from transfected cell extracts. As shown in Table 1, both the Rev-eTat and the 3C-eTat fusion protein proved highly effective at activating CAT expression directed by the pLTR/PV2/CAT expression plasmid in this human cell line. While mutation of the PV2 RNA stem-loop structure had, as expected, little or no effect on activation by the Rev-eTat fusion protein, both the Δb and the Δd mutation significantly reduced activation by 3C-eTat. In particular, the Δd mutation, which blocks 3CD binding to this RNA sequence in vitro, also entirely inhibited activation by 3C-eTat in vivo. In contrast, the Δb mutation, while significantly reducing the efficiency of the 3C/RNA interaction, nevertheless still permitted a readily detectable level of activation by the 3C-eTat fusion protein.

TABLE 1

Sequence specificity of 3C RNA binding in vivo.

| Indicator | Relative activity | |
|---|---|---|
| | Rev-eTat | 3C-eTat |
| pLTR/PV2/CAT | 68 ± 16 | 60 ± 24 |
| pLTR/PV2Δb/CAT | 46 ± 12 | 7.6 ± 2.1 |
| pLTR/PV2Δd/CAT | 54 ± 26 | 1.3 ± 0.5 |
| pLTR/PV1/CAT | 78 ± 19 | 36 ± 14 |
| pLTR/PV1Δb/CAT | 84 ± 15 | 11.4 ± 2.7 |
| pLTR/PV1Δd/CAT | 62 ± 14 | 0.9 ± 0.1 |

Relative activity measured as induced CAT activity after transfection of 293T cells with the indicated effector and indicator plasmids. Induced CAT activities are presented relative to the level observed with Rev, which here serves as a negative control. These data represent the average of three independent experiments and the observed standard deviations.

Previous in vitro studies (Andino et al, Cell 63:369–380 (1990); Andino et al, EMBO J. 12:3587–3598 (1993)) have demonstrated that the interaction of 3CD with the PV1 poliovirus 5' NCR is dependent on the presence of wild-type RNA sequences at positions 67–70 of stem-loop d and have suggested that the integrity of stem-loop b, which forms a binding site for a cellular co-factor (Andino et al, EMBO J. 12:3587–3598 (1993); Parsley et al, RNA 3:1124–1134 (1997)) is also important for efficient 3CD binding. In general, the in vivo data presented in Table 1 using PV2 RNA target sequences are consistent with these earlier in vitro data, although the readily detectable binding of PV1 3C to the PV2 5' NCR in the absence of a functional stem-loop b sequence was somewhat unexpected.

As the primary sequence of the PV2 RNA stem-loop sequence utilized in these in vivo assays differs at five sites from the PV1 RNA sequence utilized in published in vitro studies (FIG. 1B), it was desirable to examine whether these differences would affect the efficiency of the interaction with PV1 3C. Therefore, the PV1 RNA stem-loop sequence shown in FIG. 1A was precisely substituted in place of the PV2 sequence present in pLTR/PV2/CAT to generate pLTR/PV1/CAT and two equivalent mutant constructs in this PV1 RNA sequence context were then generated, termed pLTR/PV1Δb/CAT and pLTR/PV1Δd/CAT. As shown in Table 1, these PV1 based reporters in fact responded very similarly to the equivalent PV2 based reporter plasmids. In particular, the Δd mutation again entirely blocked activation by 3C-eTat while the Δb mutation resulted in a level of activation that, while readily detectable, was again significantly lower than that seen with the wild-type pLTR/PV1/CAT reporter.

To more clearly establish the degree of correlation between the in vivo assay for 3C RNA binding described above and in vitro assays for RNA binding, in vitro 3CD binding to the PV1 and PV2 RNA targets was next examined using an RNA electrophoretic mobility shift assay. As noted above, previous studies have demonstrated that 3CD forms a stable complex with PV1 RNA in the presence of a cellular factor in vitro and that the efficient formation of this ternary complex is dependent on the integrity of sequences 20–25 and 67–70 in the PV1 5' NCR. Recently, a candidate for the cellular factor that facilitates 3CD RNP complex formation, termed PCBP2, has been described (Parsley et al, RNA 3:1124–1134 (1997)). As shown in FIG. 3B, incubation of PV1 RNA (nt 1–108) or PV2 RNA (nt 1–108) with purified PCBP2 resulted in the formation of a stable complex as detected by RNA electrophoretic mobility shift analysis (lanes 2 and 14). Addition of purified recombinant 3CD to the reactions containing PCBP2 and either PV1 or PV2 RNA resulted in the formation of a ternary complex that exhibits a markedly slower electrophoretic mobility on native gels than that observed with PCBP2 alone (FIG. 3B, lanes 3 and 15). Incubation of either PV1 or PV2 RNA with 3CD alone (lanes 4 and 16) resulted in the formation of an RNA:protein complex intermediate in mobility between the PCBP2/RNA complex and the 3CD/PCBP2/RNA ternary complex. Of interest, formation of this 3CD/RNA complex was consistently observed to be more efficient with the PV2 derived RNA probe (compare lane 16 with lane 4). Importantly, introduction of the Δb mutation into either the PV1 or the PV2 RNA target still permitted the formation of low but detectable levels of this 3CD/RNA complex (lanes 7, 8, 19 and 20) although formation of both the PCBP2/RNA complex (lanes 6 and 18) and the 3CD/PCBP2/RNA complex (lanes 7 and 19) was entirely disrupted. As expected, 3CD was, however, entirely unable to interact with RNAs bearing the Δd mutation, although PCBP2 binding remained unaffected (lanes 10–12, 22–24). In total, these in vitro data demonstrate that PV1 3CD can bind to both PV1 and PV2 derived RNA targets specifically in vitro and that this interaction is detectable, even if less efficient, in the absence of the PCBP2 host cell factor. These in vitro data are, therefore, fully consistent with the in vivo data presented in Table 1.

EXAMPLE 3

Identification of Poliovirus 3C Sequences Required for RNA Binding Based on genetic studies and the solved crystal structures of picomavirus 3C proteinases, the identity of 3C residues involved in RNA binding has been proposed (Allaire et al, Nature 369:72–76 (1994); Matthews et al, Cell 77:761–771 (1994); Bergmann et al, J. Virol 71:2436–2448 (1997)). Previous studies not only suggest that 3C residues involved in RNA binding may be largely separable from those residues required for proteolytic activity but also that the putative 3C RNA binding domain is located on the opposite side of the 3C molecule relative to the proteolytic active site (Andino et al, EMBO J. 12:3587–3598 (1993); Allaire et al, Nature 369:72–76 (1994); Matthews et al, Cell 77:761–771 (1994); Bergmann et al, J. Virol 71:2436–2448 (1997)). To identify residues critical for 3C RNA binding activity in vivo, 3C-eTat expression plasmids were constructed that contain conservative single amino acid substitution mutations in residues predicted to contribute to 3C RNA binding. Plasmids encoding these mutant 3C proteins were then transfected into HeLa cells along with the pLTR/PV2/CAT reporter construct, and induced CAT activities determined. Consistent with the data in FIG. 2, cotransfection of the wild-type 3C-eTat expression plasmid with the pLTR/PV2/CAT reporter resulted in a 25-fold induction of CAT activity when compared to that observed for eTat alone (FIG. 4A). 3C-eTat fusions containing substitutions at 3C residues 89 (His to Asn), 175 (Lys to Asn), or 176 (Arg to Ser) induced levels of CAT activity that were ~8-fold, ~16-fold and ~11-fold greater, respectively, than that observed for eTat alone (FIG. 4A). The significant levels of CAT activity induced by these 3C-eTat fusions demonstrate that 3C residues His 89, Lys 175, and Arg 176 are not critical for 3C RNA binding activity in vivo. However, 3C-eTat fusions that encoded the 3C amino acid substitutions at residues 6 (Tyr to Asn), 12 (Lys to Asn), 13 (Arg to Asn), 82 (Lys to Asn), or 84 (Arg to Ser) failed to activate the pLTR/PV2/CAT reporter (FIG. 4A). Therefore, these data suggest that 3C residues Tyr 6, Lys 12, Arg 13, Lys 82 and Arg 84 are required for 3C RNA targeting in mammalian cells.

To ensure that the 3C-eTat fusion proteins mentioned above were expressed at similar levels in mammalian cells, an immunoprecipitation analysis was performed. Cells were transfected with vectors expressing 3C-eTat, 3C-R43G, or 3C-eTat fusions containing mutations in 3C. Transfected cells were then labeled with [$^{35}$S]methionine at 40 h post-transfection, and 3C-eTat proteins immunoprecipitated from the extracts of transfected cells using an 3C-specific antiserum. As shown in FIG. 4B, all 3C-eTat fusion proteins were expressed in mammalian cells at roughly comparable levels. Therefore, the defects in 3C RNA targeting observed for 3C-eTat fusions containing the Y6N, K12N, R13N, K82N or R84S mutations did not result from protein instability.

To address potential global effects on protein folding, the proteolytic activities of 3C proteinases containing all but one of the amino acid substitutions listed above were examined. The proteolytic activity of the 3C proteinase containing the R1 76S mutation was not determined because: 1) 3C-eTat fusions containing the RI 76S mutation effectively target the poliovirus 5' NCR in mammalian cells (FIG. 4), and 2) 3C proteinases containing the RI 76S mutation have been previously reported to exhibit proteolytic activity (Andino et al, EMBO J. 12:3587–3598 (1993)). The remaining mutations Y6N, K12N, R13N, K82N, R84S, H89N and K175N were introduced into a subgenomic poliovirus cDNA (pT7-P3), which encodes the P3 region of poliovirus (including 3C) located 3' of a bacteriophage T7 promoter. Plasmids were transcribed in vitro by bacteriophage T7 polymerase, and RNAs were translated in a HeLa cellular extract in the presence of [$^{35}$S]methionine. In vitro translated P3 products cleaved by the endogenously encoded 3C proteinase were then analyzed on SDS-polyacrylamide gels. As shown in FIG. 4C, all seven mutant 3C proteinases exhibited proteolytic activity, as demonstrated by the production of the 3C cleavage products 3BCD and 3CD from the P3 polypeptide precursor. Therefore, these data demonstrate that 3C residues Tyr 6, Lys 12, Arg 13, Lys 82 and Arg 84 are specifically involved in 3C RNA binding in vivo.

EXAMPLE 4

Picornavirus 3C Proteinases Display Distinct RNA Target Specificities

Previous studies have demonstrated differences in PV1 versus HRV14 3 C RNA target specificity in vitro (Walker et al, J. Biol. Chem. 270:14510–14516 (1995); Xiang et al, J. Virol. 69:3658–3667 (1995)). To directly examine the RNA target specificities of the PV1 and HRV14 3C proteinases in vivo, a reporter plasmid (pLTR/HRV14/CAT) was constructed that contains sequences derived from the HRV14 5' NCR (nt 43–75) in place of the poliovirus stem-loop d sequences (FIG. 1A). HeLa cells were cotransfected with either pLTR/ΔII/CAT, pLTR/PV2/CAT or pLTR/HRV14/CAT and plasmids expressing PV1 3C-eTat, HRV14 3C-eTat, Rev-eTat, or Rev. Induced CAT activities were then measured from extracts of transfected cells and are presented relative to those observed with Rev-eTat, which were arbitrarily set at 100 for each reporter. As shown in Table 2, both the PV1 3C-eTat and HRV14 3C-eTat fusions induced CAT expression from the pLTR/PV2/CAT reporter to levels that were ~21 percent of that observed for Rev-eTat. However, in the case of the pLTR/HRV14/CAT reporter, PV1 3C-eTat induced far lower levels of CAT activity (~6 percent of that observed for REV-eTat), while HRV14 3C-eTat induced at least comparable levels of CAT activity (~28 percent of that observed for Rev-eTat) (Table 2). Neither the PV1 nor the HRV14 3C-eTat fusions were capable of activating the pLTR/ΔII/CAT reporter, which lacks the RNA target sequences for 3C (FIG. 1B). As expected, no significant CAT activity was induced from any of these reporter plasmids by Rev alone. Therefore, consistent with previous studies (Rohll et al, J. Virol. 68:4284–4391 (1994); Walker et al, J. Biol. Chem. 270:14510–14516 (1995); Xiang et al, J. Virol. 69:3658–3667 (1995); Todd et al, Virology 229:90–97 (1997)), these data provide direct evidence that the PV1 3C and HRV14 3C proteinases exhibit differences in RNA target specificity in mammalian cells. In particular, HRV14 3C was found to interact efficiently with the poliovirus 5' NCR as well as with its cognate RNA target, while the PV1 3 C proteinase was observed to interact efficiently only with the poliovirus 5' NCR.

TABLE 2

RNA target specificity of PV1 versus HRV14 3C proteinase.

| | Relative activity[a] | | |
|---|---|---|---|
| Effector[b] | pLTR/PV2/CAT | pLTR/HRV14/CAT | pLTR)II/CAT |
| Rev | <1 | <1 | 1.0 +/− 0.25 |
| PV3C-eTat | 21 +/− 0.8 | 6 +/− 0.6 | 1.4 +/− 0.1 |

TABLE 2-continued

RNA target specificity of PV1 versus HRV14 3C proteinase.

| | Relative activity[a] | | |
|---|---|---|---|
| Effector[b] | pLTR/PV2/CAT | pLTR/HRV14/CAT | pLTR)II/CAT |
| RV3C-eTat | 21 +/− 0.5 | 28 +/− 4.7 | 1.7 +/− 0.9 |
| Rev-eTat | 100 | 100 | 100 |

[a]Relative activity measured as induced CAT activity after transfection of HeLa cells with plasmids expressing the indicated effectors and either pLTR/PV1/CAT, pLTR/HRV14/CAT, or pLTR/AII/CAT. Induced CAT activities are presented relative to that observed for Rev-eTat, which was arbitrarily set at 100 for each reporter. These data represent the average of three experiments.
[b]PV3C-eTat contains 3C sequences derived from poliovirus type-1, while RV3C-eTat contains 3C sequences derived from HRV14.

EXAMPLE 5

Activation of Nuclear mRNA Export by Human Tap

Experimental Details
Plasmid Construction

The following expression plasmids have been previously described: the mammalian expression plasmid pBC12/CMV; pcTat, pcRev, pBC12/CMV/IL-2, pBC12/CMV/β-gal (Tiley et al. 1992); the HIV-1 Rev indicator construct pDM128/CMV (Hope et al, Proc. Natl. Acad. Sci. USA 87:7787–7791 (1990); Malim et al, J. Virol. 65:4248–4254 (1991)), and equivalent constructs containing the MPMV CTE (pDM128/CTE), or a polylinker (pDM128/PL) (Bogerd et al, J. Virol. 72:8627–8635 (1998)), in place of the RRE element; a reporter plasmid containing the cat indicator gene under the control of the wild-type HIV-1 LTR (pTAR/CAT) (Tiley et al, Genes Dev. 6:2077–2087 (1992)). DNA sequences encoding amino acids 61–619 of human Tap were amplified by polymerase chain reaction (PCR) from pHA-Tap (Yoon et al, Immunity 6:571–582 (1997)) and cloned between the NcoI and XhoI sites of the pBC12/CMV plasmid to generate mammalian expression plasmid pcTap (61–619). The 60 aa N-terminal extension of the coding sequence of Tap was PCR amplified from a Clontech human T cell cDNA library using a primer that introduced an NcoI site at the 5′ end of the coding sequence and a second primer complementary to the central part of the Tap coding region. The resultant PCR product was digested with NcoI and Bsp120I, which recognizes a unique site in the Tap coding region, and inserted into the pcTap(61–619) plasmid digested with NcoI and Bsp120I. The resultant plasmid pcTap encodes the complete human Tap cDNA sequence. Truncated forms of Tap were amplified by PCR and cloned into the NcoI and XhoI site of pBC12/CMV. The full length tat gene was amplified by PCR with primers that introduced flanking NcoI sites and then ligated into NcoI digested pcTap series plasmids to generate plasmids that express chimeric proteins consisting of Tat fused to full length or mutant Tap proteins. Sequences encoding aa 129–131 of Tap in pcTat-Tap(61–619) were mutated using the Quickchange kit (Stratagene) to GCGGCCGCC, which encodes a triple alanine, to generate pcTat-Tap $^{KYD-AAA}$(61–619). This plasmid was then digested with NcoI and religated to remove tat coding sequence, resulting in pcTap$^{KYD-AAA}$(61–619). The yeast expression vector pVP16 has been described (Bogerd et al, J. Virol. 67:5030–5034 (1993)). A triple HA tag was inserted in frame to the VP16 coding sequence, into the BglII and EcoRI sites of the polylinker sequence in pVP16, to generate the cloning vector pVP16-HA. Sequences encoding full length or truncated forms of Tap were inserted into the EcoRI and XhoI sites of pVP16-HA to generated plasmids expressing Tap proteins fused to the VP16 transcription activation domain and the HA Tag. Full length and half CTE fragment were amplified by PCR and then inserted as blunt-ended DNA fragments into a SmaI site in the yeast plasmid pIII/MS2 (Sengupta et al, Proc. Natl. Acad. Sci. USA 93:8496–8501 (1996)) to generated yeast three-hybrid plasmids that express hybrid MS2-CTE RNAs under the control of the RNase P1 promoter. CTE fragments with flanking BamHI sites at each end were cut from these plasmids and inserted into the BglII site of pDM128/CMV (Malim et al, J. Virol. 65:4248–4254 (1991)), as well as the BamHI site present in the in vitro transcription plasmid pGEM-3fZ. Mutant/variant CTE constructs were generated by using the Quick change site-directed mutagenesis kit (Stratagene). Reporter plasmids for mammalian CTE binding assays were generated by replacing the TAR element in pTAR/CAT with wild-type or mutant/variant CTE elements. CTE fragments were PCR amplified from pDM128/CMV based CTE constructs using primers containing unique BglII and SacI sites and inserted into pTAR/CAT digested with the same enzymes.

The DNA sequence in pDM128/CMV that flanks the 3′ splice site, which is derived from pgTAT (Malim et al, Nature 338:254–257 (1989)), was PCR amplified with primers containing EcoRI and KpnI sites and cloned into these two sites in pGEM3fZ (Promega) to generate the in vitro transcription plasmid pT7-RPA. In vitro transcription of pT7-RPA using T7 polymerase generated an antisense RNA fragment, that starts at nt 3450 of pgTAT and then extends through the predicted 3′ splice site, at nt 3349, to end at nt 3293.

Cell Culture and Transfection

Human 293T and quail QC1-3 were maintained as previously described (Cullen et al, Proc. Natl. Acad. Sci. USA 80:2946–2950 (1983); Bogerd et al, J. Virol. 72:8627–8635 (1998)) and transfected using lipofectamine (Life Technologies) or DEAE-Dextran (Cullen et al, Proc. Natl. Acad. Sci. USA 80:2946–2950 (1983)), respectively. All transfections were performed on cell cultures in 35 mm plates. Levels of DNA used in each transfection experiment are given in the relevant figure legend, with pBC12/CMV/β-gal included as an internal control. In all transfection experiments, CAT enzyme levels were determined 48 hr after transfection, as previously described, and normalized to the level of β-gal activity present in the cell lysate (Bogerd et al, J. Virol. 72:8627–8635 (1998)).

Yeast Three-hybrid Assays

Saccharomyces cerevisiae L40-coat cells (Sengupta et al, Proc. Natl. Acad. Sci. USA 93:8496–8501 (1996)) were transformed with a pIII/MS2-based hybrid RNA expression plasmid and pVP16-HA-Tap (or various truncated mutants of Tap). Transformants were selected on media lacking uracil and leucine. Overnight cultures of pooled transformants were suspended in β-gal assay buffer, normalized to optical density, and β-gal activities assayed as previously described (Bogerd et al, J. Virol. 67:5030–5034 (1993)).

In vivo Randomization/Selection of Tap Binding Sequences

The randomized half CTE library was generated by large scale site directed mutagenesis of the mutant half-CTE yeast three-hybrid analysis construct pIII/MS2/½CTE-M2 using the following primers with randomized sequence from nucleotide 8070 to 8076 of the MPMV CTE:

5′-CCCCCGGATCCACTAACCNNNNNNNGGAGG GCCGTCAAAGCTA-3′ (SEQ ID NO:1)

5'-TAGCTTTGACGGCCCTCCNNNNNNNGGTTA GTGGATCCGGGGG-3' (SEQ ID NO:2)

The mutagenesis products were transformed into Escherichia coli DH5α. After selection for ampicillin-resistant transformants, the randomized library was found to consist of about 50,000 independent clones. DNA from the library was pooled and co-transformed with pVP16-HA-Tap (61–619) into yeast L40 coat cells. The transformed yeast cells were plated on uracil- and leucine-deficient (Ura⁻ Leu⁻) plates covered with a Hybond-N nylon membrane (Amersham). After 3 days of growth, the nylon membrane with yeast colonies was lifted from the plate, frozen at 140° C. for 10 min, and then thawed at room temperature. An in situ β-gal assay was carried out by placing the nylon membrane on filter papers soaked in 0.5xZ buffer (Blair et al J. Virol. 68:3803–3808 (1994)) with 0.3 mg of chlorophenolred-D-galactopyranoside (CPRG; Boehringer Mannheim) per ml and 0.1% (vol/vol) 2-mercaptoethanol. After 1 hr of incubation at room temperature, colonies that turned blue were picked and recovered on Leu⁻ Ura⁻ plates, and the yeast indicator plasmids harboring candidate Tap binding site variant sequences rescued after overnight culture. A second yeast transformation and β-gal assay were then performed with the selected indicator plasmids, together with either pVP16-HA-Tap(61–619) or the parental plasmid pVP16, to quantify the level of transactivation by Tap and to identify any false (i.e., Tap-independent) positive clones. The CTE sequences in the true-positive clones were then obtained by ABI automatic cycle sequencing (PE Applied Biosystems).

Gel Shift Analysis

GST-fusion proteins, containing full length or truncated forms (aa 61–619 and aa 61–372) of Tap were expressed and purified on glutathione affinity resin as previously described (Grüter et al, Mol. Cell 1:649–659 (1998)). The wild-type and various mutant/variant CTE RNA probes were labeled with [α-$^{32}$P]CTP by Riboprobe in vitro transcription system (Promega) and the total isotope incorporation determined by scintillation counting after column purification. The binding reaction was carried out with ~10$^4$ cpm (~0. 1 ng) of the probe and 25 ng of GST-Tap fusion protein in 20 μl of binding buffer (150 mM KCl, 10 mM HEPES [pH 7.6], 0.5 mM EGTA, 2 mM MgCl$_2$, 1 mM DTT and 10% glycerol) containing 4 μg of rRNA and 1 μg of yeast tRNA. Binding was allowed to proceed for 20 min at 4° C. and the reaction products resolved on a 5% (40:1) native polyacrylamide gel and visualized by autoradiography. Unlabeled competitor RNAs were synthesized using the RiboMax large scale RNA production system (Promega). For competition experiments, competitor RNAs were added at a 200-fold molar excess over the labeled probe fragment and incubated with GST-Tap(61–372) for 10 min before addition of the probe. The results of competition experiments were quantitated with a PhosporImager and Image QuaNT software (Molecular Dynamics).

RNA Isolation and Ribonuclease Protection Assay (RPA)

Quail QCl-3 cells (six well 35 mm plates) were transfected with 100 ng of pcTap or pBC12/CMV, 25 ng of pDM128/CTE and 400 ng of pBC12/CMV. Nuclear and cytoplasmic RNAs were fractionated from QCl-3 cells at 72 hr after transfection, and purified by SV Total RNA Isolation System (Promega) or RNeasy Cytoplasmic RNA Isolation Kit (Qiagen), respectively. RPA analysis was performed using the Hyspeed RPA kit (Ambion) following the manufacturer's protocol. The RNA probe used in this assay was generated by in vitro transcription of plasmid pT7-RPA linearized at the HindIII site, using the Riboprobe kit (Promega). The input probe is 208 nucleotides in length, with additional "tag" sequence derived from vector sequence between KpnI and HindIII sites to allow the full-length, input probe to be distinguished from probe fragments rescued by the unspliced and spliced mRNA transcripts, which have a predicted length of 158 and 102 nucleotides, respectively.

Results

Human Tap has previously been reported to be a 559 amino acid (aa) protein, with a predicted size of ~63 kDa (Yoon et al, Immunity 6:571–582 (1997)), and this was the size Tap protein utilized in the previous report implicating Tap as a CTE cofactor (Grüter et al, Mol. Cell 1:649–659 (1998)). However, recently deposited rat and mouse Tap cDNA sequences, while highly homologous to the human sequence, predict a Tap protein of 618 aa in length due to a 59 aa amino terminal extension (Tannoch et al, GenBank Accession number AF093140 (1988)). Therefore, 5' flanking sequences were cloned adjacent to the published human Tap initiation codon and it was observed that this open reading frame also extends 5' to the published sequence, in this case predicting a 60 aa extension that is 92% identical to the deposited mouse Tap sequence. Preliminary western analysis has confirmed that the endogenous human Tap protein migrates at ~-70 kDa, the predicted size encoded by this extended Tap open reading frame. While most experiments were therefore performed utilizing the longer "1/619" form of Tap, the previously published "61/619" form of Tap was also included in many experiments as the possibility that this shorter form of Tap also exists in vivo could not be excluded. The extended human Tap coding sequence has been deposited with GenBank under accession number AF112880.

The predicted structure of the MPMV CTE RNA export sequence is shown in FIG. 6. The helical nature of the CTE has been shown (Tabernero et al, J. Virol. 70:5998–6011 (1996); Ernst et al, RNA 3:210–222 (1997)) to largely serve a structural role in the appropriate presentation of two RNA loops, designated A and B in FIG. 6, that are perfect 180° mirror images of one another. While both of these loops are essential for CTE function in primate cells, one loop is sufficient for CTE function in Xenopus oocytes (Pasquinelli et al, EMBO J. 16:7500–7510 (1997); Tabernero et al. 1997; Grüter et al, Mol. Cell 1:649–659 (1998)). The reason for this difference between Xenopus oocytes and cultured primate cells is not currently known.

Tap Binds the CTE Specifcally in Vivo

While a specific Tap:CTE interaction has been previously demonstrated in vitro (Grüter et al, Mol. Cell 1:649–659 (1998)), it was desirable to confirm that this interaction would also occur in vivo. Therefore, it was first asked whether the 1/619 form of Tap would bind the full-length MPMV CTE, or to a half CTE RNA target consisting of the apical half of the CTE (FIG. 6), in the yeast three hybrid RNA:protein interaction assay (Sengupta et al, Proc. Natl. Acad. Sci. USA 93:8496–8501 (1996)). As specificity controls, CTE mutants were used bearing a single A to G mutation in loop A (M1-A), loop B (M1-B) or both loops (M1-AB). All three of these mutants are defective for CTE-dependent RNA export in human cells (see below).

As shown in Table 1, Tap proved able to specifically interact with the full-length CTE but not with an antisense CTE, the HIV-1 TAR element or an iron response element (IRE) RNA target. As predicted from earlier in vitro work (Grüter et al, Mol. Cell 1:649–659 (1998)), Tap also bound the half CTE RNA target and to the two full-length CTE RNAs (M1-A and M1-B) bearing only one functional CTE loop. However, Tap did not bind the CTE mutant, termed M1-AB, in which both loops had been inactivated by single base mutations (FIG. 6). An extensive mutation introduced into the terminal CTE loop (M-L), which is not required for CTE function, also had little effect on Tap binding to either the full-length or half CTE.

TABLE 3

Interaction of Tap with the MPMV CTE in yeast cells

|  |  | β-gal activity (mOD/ml) | |
|---|---|---|---|
|  |  | VP16-Tap | VP16 |
|  | IRE | <4 | <4 |
|  | TAR | <4 | <4 |
|  | CTE | 602 | 11 |
|  | CTE-AS | <4 | <4 |
|  | M1-A | 406 | <4 |
| CTE | M1-B | 148 | <4 |
|  | M1-AB | <4 | <4 |
|  | M-L | 597 | <4 |
|  | ½ CTE | 1691 | 21 |
| ½ CTE | M-L | 509 | 15 |
|  | M1 | <4 | <4 |

The ability of human Tap to bind to wild-type and mutant forms of the MPMV CTE was analyzed using the yeast three hybrid RNA: protein interaction assay. The indicated levels of β-gal activity, induced upon interaction of a fusion protein consisting of the VP16 activation domain fused to the full-length Tap protein with the indicated RNA targets, represent the average of three independent experiments. Controls included the HIV-1 TAR element, a human iron response element (IRE) and the antisense CTE (CTE AS). The single nucleotide M1 mutation, which inactivates CTE function, is shown in FIG. 6 and was introduced into loop A (M1-A), loop B (M1-B) or both CTE loops (M1-AB). The terminal CTE loop mutation M-L, which does not block CTE function, is also shown in FIG. 6.

The yeast data presented in Table 3 confirm published in vitro data showing that specific Tap binding to the CTE requires only one intact loop (Grüter et al, Mol. Cell 1:649–659 (1998)). Yet, CTE function in primate cells requires both loops (Tabernero et al. 1997). One possible explanation for this discrepancy is that Tap binding in primate cells also requires both loops. To test this hypothesis, a recently described (Blair et al, RNA 4:215–225 (1998)) mammalian RNA:protein binding assay was used that takes advantage of the unique ability of the HIV-1 Tat protein to activate HIV-1 long terminal repeat (LTR) dependent transcription via an RNA target. Normally, Tat interacts with an RNA stem-loop structure, termed TAR, found just 3' to the HIV-1 LTR transcription start site. However, Tat will also activate the LTR when it is recruited to a heterologous RNA target, substituted in place of TAR, after fusion to the appropriate RNA binding protein (Selby. and Peterlin, Cell 62:769–776 (1990); Tiley et al, Genes Dev. 6:2077–2087 (1992)). Therefore, wild-type or mutant forms of the CTE were substituted in place of the TAR element present in the HIV-1 LTR and the level of activation observed upon co-transfection of a Tat-Tap fusion protein was measured.

As shown in FIG. 7, Tat-Tap co-expression gave rise to an ~20 fold increase in the level of expression of a cat indicator gene linked to an HIV-1 LTR in which TAR had been substituted by either the complete CTE or half CTE. This is approximately one half the level of activation observed upon coexpression of either Tat or the Tap-Tat fusion protein with a similar wild-type HIV-1 LTR based indicator construct. The activation of the CTE-containing HIV-1 LTR indicator plasmid by Tap-Tat was specific in that it was blocked by the M1-AB mutation of the complete CTE, and by the M1-B mutation in the half CTE, and was not detected when Tat alone or Tap alone was expressed (FIG. 7). As in the case of the yeast three hybrid assay, mutation of the terminal CTE loop (M-L) had little effect on Tap binding, while mutation of either internal CTE loop alone (M1-A or M1-B) resulted in partial activity. It was therefore concluded that Tap is able to bind the CTE specifically in both yeast and human cells and that this interaction requires a single intact CTE loop.

Tap Contains a Novel RNA Binding Domain that Includes a Leucine Rich Region (LRR) Motif The Tap protein does not contain an obvious RNA binding motif and it was therefore desired to define the sequences in Tap that were necessary and sufficient for CTE RNA binding. In the yeast three hybrid assay, the 61/619 form of human Tap, previously thought to constitute full-length Tap, retained wild-type RNA binding activity while deletion mutants consisting of Tap residues 61/372 or 80/372 actually showed significantly enhanced CTE RNA binding (FIG. 8A). This result may be in part explained by the ~3–4 fold higher level of expression of these latter two Tap deletion mutants, as detected by western blot analysis. Further deletion of residues 80 to 101 (in 102/372) or 351 to 372 (in 61/350) respectively either abolished or severely inhibited RNA binding.

It was next asked whether the yeast data presented in FIG. 8A were predictive of Tap binding in mammalian cells. As shown in FIG. 8B, residues 61 to 372 of Tap indeed showed wild-type CTE binding in human cells while residues 80 to 372 showed slightly reduced CTE binding. As in the case of yeast cells, residues 61 to 350 of Tap retained partial CTE binding activity while residues 61/329 and 102/372 were inactive. A missense mutation introduced into Tap residues 129 to 131, termed Tap(KYD-AAA), was observed to also inactivate CTE binding by Tap. Analysis of the Tat activity of each of the Tat:Tap fusion proteins shown in FIG. 8B, using a wild-type, HIV-1 LTR based indicator construct, showed that all of these proteins were expressed in a functional form in the nucleus of transfected human 293T cells. These data in human cells (FIG. 8B) therefore closely mirror the data obtained in yeast cells (FIG. 8A) except that enhanced CTE binding by the 61/372 and 80/372 Tap mutants is seen only in the latter system.

To confirm that Tap residues 61/372 are indeed fully sufficient for CTE binding, the CTE binding properties of glutathione-S-transferase (GST) fusion proteins containing full-length Tap, Tap residues 61/619 or Tap residues 61/372 were analyzed using an in vitro RNA gel-shift assay. As shown in FIG. 9A, all three Tap proteins bound to the full-length wild-type CTE, in each case giving rise to two shifted bands that may reflect binding to one or both CTE loops. In contrast, none of these three Tap proteins proved able to bind a full-length CTE probe bearing the M2 mutation in both loop A and loop B (FIG. 9A). It was therefore concluded that Tap contains a novel RNA binding domain that includes an unusual leucine-rich repeat (LRR) motif first noted by Segref et al, EMBO J. 16:3256–3271 (1997) in their analysis of Mex67p, the yeast homolog of Tap.

Ability of CTE Mutants to Bind Tap Correlates with CTE Activity in Human Cells

While it has previously been shown that the ability of CTE mutants to bind Tap correlates with CTE function in Xenopus oocytes (Grüter et al, Mol. Cell 1:649–659 (1998)), this earlier analysis used a rather severe set of, predominantly, deletion mutants, none of which were intermediate in either RNA export activity or Tap binding. To generate such intermediate CTE mutants, the yeast three-hybrid assay was utilized to select mutant forms of the CTE that retained Tap binding activity from a pool of randomized CTE sequences. Starting from a yeast construct expressing a half CTE bearing an inactivating loop mutation (mutant M2, see Table 4), seven residues forming the 5' side of loop B (5'-UAAGACA-3') were randomized and then loop variants were selected that retained the ability to bind Tap in the yeast three hybrid assay, as shown by expression of the β-gal indicator gene.

TABLE 4

Interaction of Tap with CTE mutants and selected CTE variants in yeast and human cells

| Clone | Sequence | Relative Tap binding activity | |
|---|---|---|---|
| | | in yeast cells | in human cells |
| WT(x8) | '-UAAGACA-3' | 100 | 21.6 |
| V1(x6) | UAA<u>A</u>ACA | 33 | 2.8 |
| V2(x5) | UAAG<u>C</u>CA | 69 | 4.8 |
| V3(x2) | UA<u>GG</u>ACA | 25 | 2.7 |
| V4(x2) | <u>GG</u>A<u>AAA</u> | 50 | ≦1 |
| M2 | UAA<u>AGU</u>A | <1 | ≦1 |
| M3 | UA<u>AC</u>ACA | <1 | ≦1 |
| M4 | UAAG<u>G</u>CA | 16 | 1.6 |
| M5 | UA<u>U</u>GACA | 9 | 1.4 |

Seven nucleotides that form the 5' side of CTE loop B were randomized in the context of a 1/2 CTE bearing the inactivating M2 mutation. Variants that retained Tap binding were then selected using the three hybrid screen in yeast cells. The five recovered sequences, together with the number of times each was recovered, are given at the top of the table as WT and the variants V1 to V4. Several CTE mutants (M2 to M5) were also constructed and are given in the lower part of the table. Relative binding of these ½ CTE variants and mutants to full-length human Tap was determined in yeast, as described in Table 3, and in human 293T cells, using the Tat-based RNA:protein interaction assay described in FIG. 7. Yeast data are given as a percentage of the activity of the wild-type CTE averaged over several experiments. Human Tap binding data are given as relative activation of CAT expression by Tap-Tat and represent the average of three independent transfection experiments. Variant V1has previously been reported as mutant #30, and mutant M4 as mutant #31, by Tabernero et al, J. Virol. 70:5998-6011 (1996), who reported both as partially active CTE mutants.

As shown in Table 4 this randomization led to the recovery of five CTE sequences able to interact with Tap, all of which were recovered two or more times. In addition to the wild-type CTE sequence, four CTE variants (V1 to V4, Table 4) were recovered that showed a level of Tap binding that varied between 69% and 25% of that seen with the wild-type CTE, thus strongly suggesting that the wild-type CTE has the optimal RNA sequence for Tap binding. Variants V1 to V3 were found to differ from the wild-type sequence by only one nucleotide while V4 differed at four out of seven positions (Table 4).

To further confirm that most single residue mutations introduced into the CTE loop would not be consistent with effective Tap binding, single nucleotide changes at loop positions 2 (M5), 3 (M3) or 4 (M4) were introduced (see FIG. 6) and these were compared to the selected CTE variants V3, V1 and V2, which are respectively modified at these same positions. As shown in Table 4, CTE mutant M3 was unable to bind Tap while mutants M5 and M4 retained, respectively, 9% or 16% of wild-type binding activity. It was hypothesized that these latter two mutants were not recovered in the randomization/selection screen because their activity falls below the minimum level necessary for detection in the relatively insensitive in situ assay for β-gal expression.

To confirm the relevance of these yeast RNA binding data to the mammalian system, the level of Tap binding to each of these CTE mutants was measured, in the one half CTE context, using the mammalian RNA:protein binding assay described in FIG. 8B. As shown in Table 4, there was excellent agreement between these two assays for all CTE variants except V4. Specifically, CTE variant V2 gave strong Tap binding, variants V1 and V3 gave modest binding, M4 and M5 gave weak binding while mutants M2 and M3, as well as variant V4, gave no detectable binding. The clear discrepancy between the yeast and mammalian binding assays in the case of V4 was particularly surprising given the close similarity in the data recovered for all other CTE variants. After carefully confirming the sequence integrity of the relevant clones, it was hypothesized that this difference might reflect either the presence of a facilitating yeast gene product or the presence, in mammalian cells, of a gene product that blocks Tap binding to V4. To distinguish between these two possibilities, a competitive RNA gel shift analysis was used to compare binding by these various CTE variants in vitro. As shown in FIG. 9B, strong Tap binding by V2, significant binding by V1 and V3 and little or no binding with V4 or with the CTE mutants M3, M4 and M5 were observed. It was therefore concluded that the interaction of V4 with Tap in yeast cells is likely to be an artifact that is not reproduced either in vitro or in a mammalian cell based RNA binding assay.

The primary purpose of generating the CTE mutants shown in Table 4 was to ask whether Tap binding activity closely correlated with CTE function in primate cells. The pDM128/CTE indicator plasmid, which encodes the cat indicator gene and wild-type CTE located between functional 5' and 3' splice sites, has been previously described (Bogerd et al, J. Virol. 72:8627–8635 (1998); Otero et al, J. Virol. 72:7593–7597 (1998)). Because splicing removes the cat open reading frame, efficient CAT expression is dependent on the nuclear export of the unspliced cat mRNA, i.e. on CTE function. As shown in FIG. 10, and previously described elsewhere (Bogerd et al, J. Virol. 72:8627–8635 (1998)), the wild-type CTE indeed induced a significant increase in CAT expression relative to a plasmid, termed pDM128/PL, that is identical except for the lack of a CTE. Therefore, a set of pDM 128/CTE variants were next constructed containing the CTE mutations described in Tables 3 and 4, in most cases introduced into both CTE loops, and measured their biological activity in transfected human cells was measured. As shown in FIG. 10, there was indeed a close correlation between Tap binding activity and CTE biological activity with the exception, noted above, that CTE mediated RNA export requires two intact loops whereas Tap binding requires only one functional loop. Specifically, it was observed that the V2 and M-L mutants displayed strong partial activity, while the V1, V3 and possibly M4 CTE mutants displayed weak activity. All other CTE mutants, including V4, proved to be essentially inactive.

Quail Cells are Rendered Permissive for CTE Function Upon Expression of Human Tap The unequivocal demonstration that Tap is indeed the critical cofactor for CTE function has been difficult due to the lack of a tissue culture system where the CTE is inactive. The only system where the effect of Tap on CTE mediated RNA export has been reported is Xenopus oocytes, which are partly permissive for CTE function but give enhanced activity upon microinjection of recombinant Tap protein (Grüter et al, Mol. Cell 1:649–659 (1998)). In primate cells, in principle the most relevant system for studying CTE function, Tap overexpression does not enhance the biological activity of the CTE, as shown in FIG. 11A. A search was therefore undertaken for a cell line that was non-permissive for CTE function but that could be genetically complemented by the human tap gene. As shown in FIG. 11B, the quail cell line QCl-3 gives precisely this phenotype. In the absence of co-transfected human Tap, the MPMV CTE gives a ≦2 fold effect on the expression of the cat indicator gene present in the pDM128/CTE indicator plasmid. However, expression of either full-length human Tap, or of the shorter 61/619 form of Tap, resulted in a dramatic CTE dependent increase in CAT expression. To show that this effect was indeed at the level of nuclear RNA export, total RNA was isolated from the nuclear and cytoplasmic fractions of QCl-3 cells transfected with pDM128/CTE in the presence or absence of co-expressed Tap. As shown in FIG. 11C, Tap had little or no effect on the relative level of spliced and unspliced RNA expressed in the nuclear fraction (lanes 1 and 2) but markedly enhanced the expression of the unspliced cat MRNA in the quail cell cytoplasm (compare lanes 3 and 4). This is precisely the result expected for a nuclear RNA export factor and highly comparable to data previously reported for CTE or Rev/RRE dependent mRNA export in primate cells (Malim et al, Nature 338:254–257 (1989); Bray et al, Proc. Natl. Acad. Sci. USA 91:1256–1260 (1994)).

In FIG. 10, it was reported that the biological activity of various CTE variants in transfected human cells, in the absence of co-transfected Tap, and shown that there was a good correlation between the ability of these CTE variants to function in RNA export and their ability to bind to Tap in mammalian cells (Table 4) or in vitro (FIG. 9B). As shown in FIG. 12A, these CTE variants and mutants gave a similar pattern of biological activity in QCl-3 cells upon co-transfection of the human tap gene. Specifically, CTE variant V2 and the M-L mutant were highly active, variants V1 and V3 moderately active and mutant M4 weakly active, with all other CTE mutants inactive. Importantly, the half CTE also proved entirely inactive, as did forms of the full-length CTE bearing the single nucleotide M1 mutation in either the A or B loop (FIG. 12A). Therefore, it is apparent that quail cells are similar to primate cells (FIG. 10), and dissimilar from Xenopus oocytes (Pasquinelli et al, EMBO J. 16:7500–7510 (1997); Grüter et al, Mol. Cell 1:649–659 (1998)), in that both CTE loops are required for CTE function.

The Tap RNA Binding Motif is not Sufficient for Tap Function in Quail Cells

In FIG. 8 and FIG. 9A, it was observed that residues 61 to 372 of Tap are fully sufficient for CTE RNA binding. To examine whether they are also sufficient to mediate CTE function, the ability of Tap(61–372) to rescue CTE function in quail cells was examined. As shown in FIG. 12B, Tap residues 61–372 in fact proved entirely inactive. Because the data on Tap RNA binding in the mammalian nucleus shown in FIG. 8B utilized a Tat-Tap fusion protein, we also tested the activity of these fused forms of Tap to rescue CTE function, in case Tat was necessary to provide some function, such as a nuclear localization sequence, in cis. As shown in FIG. 12B, Tat-Tap(61–372), unlike Tat-Tap and Tat-Tap(61 "619), also failed to rescue CTE function in quail cells despite showing an essentially wild-type level of CTE binding in the mammalian cell-based RNA binding assay (FIG. 8B). As expected, the KYD-AAA missense mutation, which blocks CTE binding by Tap (FIG. 8B), also blocked rescue of CTE function by Tap.

If Tap(61–372) is able to bind the CTE, but then unable to mediate CTE nuclear export, it should act as a CTE-specific dominant negative mutant of Tap. As shown in Table 5, this is indeed the case. In particular, overexpression of Tap(61–372) significantly inhibited the ability of the wild-type Tap protein to rescue CTE function in QCl-3 cells but had no effect on Rev dependent nuclear RNA export in these same cells. The Tap(KYD-AAA) mutant, which lacks a functional RNA binding motif but presumably retains any Tap effector domain, exerted a more modest dominant negative phenotype that was also specific for Tap function. As perhaps predicted by the lack of any effect of a transfected wild-type Tap construct in human cells, it was not possible to observe any significant effect of either Tap mutant on CTE function in human cells.

TABLE 5

Specific inhibition of Tap, but not Rev function by Tap mutants

| | | CAT activity | | | |
|---|---|---|---|---|---|
| | | RRE | | CTE | |
| | Neg | 1040 | (6 ± 1) | 2172 | (10 ± 2) |
| | Tap or Rev (25 ng) | 16937 | (100 ± 13) | 22517 | (100 ± 7) |
| | Tap | 18939 | (112 ± 21) | 24769 | (110 ± 12) |
| Competitor | Tap(61-372) | 15105 | (89 ± 9) | 6176 | (27 ± 4) |
| (500 ng) | Tap$^{KYD-AAA}$ (61-619) | 15701 | (93 ± 12) | 11302 | (50 ± 7) | pDM128 based indicator constructs (25 ng) containing either the HIV-1 RRE or the MPMV CTE were transfected into QCl-3 cells together with 25 ng of pcRev, pcTap or the pBC12/CMV control plasmid and 25 ng of pBC12/CMV/β-gal. The level of activation obtained upon cotransfection of an additional 500 ng of the pBC12/CMV control is compared to the level observed when pBC12/CMV is replaced by 500 ng of a plasmid expressing wild-type Tap, the isolated Tap RNA binding motif (Tap 61-372) or a Tap protein unable to bind the CTE (Tap$^{KYD-AAA}$). Data are presented both as a single representative experiment and, in brackets, as the average of three independent experiments and are normalized using the pBC12/CMV/β-gal internal control.

All documents cited above are hereby incorporated in their entirety by reference. One skilled in the art will appreciate from a reading of this disclosure that various changes in form and detail can be made without departing from the true scope of the invention.

What is claimed is:

1. A method for screening a test compound for its ability to modulate a RNA:protein interaction comprising:
   i) preparing a reporter construct comprising, in order, a Tat-responsive promoter operably linked to a sequence encoding a heterologous RNA binding site, and an indicator gene,
   ii) preparing an effector construct comprising a promoter operably linked to a nucleic acid sequence encoding a fusion protein comprising a Tat protein activation domain and a protein cognate of said heterologous RNA binding sites,
   iii) introducing said reporter construct and said effector construct into a vertebrate host cell and culturing said host cell in the presence and absence of said test compound, and
   iv) measuring the level of expression of said indicator gene in the presence and absence of said test compound, a difference in the level of expression of said indicator gene in the presence of said test compound, as compared to the level of expression of said indicator gene in the absence of said test compound, being indicative of a test compound that modulates interaction of said heterologous RNA binding site with said protein cognate.

2. The method according to claim 1 wherein said TAT responsive promoter is a lentivirus LTR.

3. The method according to claim 1 wherein the reporter construct comprises a minimum Tat-responsive LTR promoter.

4. The method according to claim 1 wherein the reporter construct further comprises an internal ribosome entry site between the heterologous RNA binding site and the indicator gene and in operable linkage therewith.

5. The method according to claim 1 wherein the reporter construct comprises the RNA stem-loop binding site for polio and rhino-viral 3C proteins, or the RNA binding site from a picornavirus.

6. The method according to claim 1 wherein the effector construct comprises a cytomegalovirus intermediate early promoter, a SV40 early promoter or a retroviral LTR promoter.

7. A vertebrate host cell comprising:
   i) a reporter construct comprising, in order, a Tat-responsive promoter functional in said host cell operably linked to a sequence encoding a heterologous RNA binding site, and an indicator gene, and ii) an effector construct comprising a promoter functional in said host cell operably linked to a nucleic acid sequence encoding a fusion protein comprising a Tat protein activation domain and a protein cognate of said heterologous RNA binding site, wherein said host cell expresses the protein product of said indicator gene.

8. The host cell according to claim 7 wherein said TAT responsive promoter is a lentivirus LTR.

9. The host cell according to claim 7 wherein wherein the reporter construct comprises a minimum Tat-responsive LTR promoter.

10. The host cell according to claim 7 wherein the reporter construct further comprises an internal ribosome entry site between the heterologous RNA binding site and the indicator gene and in operable linkage therewith.

11. The host cell according to claim 7 wherein said host cell is a mammalian cell.

12. The host cell according to claim 11 wherein said host cell is a human cell.

13. The host cell according to claim 11 wherein said host cell is a human fibroblast cell, a human T-cell, a rodent cell or a monkey cell.

14. The method according to claim 7 wherein the reporter construct comprises the RNA stem-loop binding site for polio and rhino-viral 3C proteins, or the RNA binding site from a picornavirus.

15. The method according to claim 7 wherein the effector construct comprises a cytomegalovirus intermediate early promoter, a SV40 early promoter or a retroviral LTR promoter.

16. A kit comprising a reporter construct disposed with a container means and an effector construct disposed within a container means wherein the reporter construct comprising, in order, a Tat-responsive promoter operably linked to a site suitable for insertion of a sequence encoding a heterologous RNA binding site, and an indicator gene, and the effector construct comprising a promoter operably linked to a nucleic acid sequence encoding a Tat protein activation domain, said nucleic acid sequence comprising a site 3' or 5' to said Tat protein activation domain encoding sequence, suitable for insertion of a sequence encoding a protein cognate of said heterologous RNA binding site.

17. The kit according to claim 16 wherein said TAT responsive promoter is a lentivirus LTR.

18. The kit according to claim 16 wherein the reporter construct comprises a minimum Tat-responsive LTR promoter.

19. The kit according to claim 16 wherein the reporter construct further comprises an internal ribosome entry site between the heterologous RNA binding site and the indicator gene and in operable linkage therewith.

20. The kit according to claim 16 wherein the reporter construct comprises the RNA stem-loop binding site for polio and rhino-viral 3C proteins, or the RNA binding site from a picornavirus.

21. The kit according to claim 16 wherein the effector construct comprises a cytomegalovirus intermediate early promoter, a SV40 early promoter or a retroviral LTR promoter.

* * * * *